US009155571B2

(12) United States Patent
Thommen et al.

(10) Patent No.: US 9,155,571 B2
(45) Date of Patent: Oct. 13, 2015

(54) MINIMALLY INVASIVE INTERSPINOUS PROCESS SPACER IMPLANTS AND METHODS

(75) Inventors: Daniel Thommen, Liestal (CH); Markus Weber, Balterkinden (CH); Jacques Teisen, Zurich (CH); Markus Kraft, Frenkendorf (CH); Florian Kaufmann, Sissach (CH); Markus Hunziker, Aarau (CH); Felix Aschmann, Basel (CH); Stefan Saladin, Oltingen (CH); Martin Oswald, Meilen (CH); Roman Randegger, Aarburg (CH)

(73) Assignee: DePuy Synthes Products, Inc., Raynham, MA (US)

( * ) Notice: Subject to any disclaimer, the term of this patent is extended or adjusted under 35 U.S.C. 154(b) by 581 days.

(21) Appl. No.: 12/940,125

(22) Filed: Nov. 5, 2010

(65) Prior Publication Data

US 2011/0190817 A1    Aug. 4, 2011

Related U.S. Application Data

(60) Provisional application No. 61/258,632, filed on Nov. 6, 2009.

(51) Int. Cl.
*A61F 2/44*   (2006.01)
*A61B 17/70*  (2006.01)
(Continued)

(52) U.S. Cl.
CPC ............. *A61B 17/7065* (2013.01); *A61B 19/54* (2013.01); *A61B 2017/00557* (2013.01)

(58) Field of Classification Search
CPC ................................................ A61B 17/7065
USPC ....................... 606/249; 623/17.16
See application file for complete search history.

(56) References Cited

U.S. PATENT DOCUMENTS

| 4,364,392 A | 12/1982 | Strother et al. |
| 4,441,495 A | 4/1984 | Hicswa |

(Continued)

FOREIGN PATENT DOCUMENTS

| WO | 2005009300 | 2/2005 |
| WO | 2008/056237 | 5/2005 |

(Continued)

OTHER PUBLICATIONS

Notification of Transmittal of The International Search Report and Written Opinion, dated Apr. 19, 2011, received from the European Patent Office.

(Continued)

*Primary Examiner* — Eduardo C Robert
*Assistant Examiner* — Stuart S Bray
(74) *Attorney, Agent, or Firm* — Meunier Carlin & Curfman LLC

(57) ABSTRACT

An interspinous process spacer for implantation in an interspinous space between a superior spinous process and an inferior spinous process includes a balloon-like body, a first deployable protrusion and a second deployable protrusion. The body has a distal end, a proximal end and a longitudinal axis extending between the proximal and distal ends. The spacer is arrangeable in an unexpanded configuration and an expanded configuration. The first deployable protrusion is mounted proximate the proximal end and the second deployable protrusion is mounted proximate the distal end. The first and second deployable protrusions are oriented generally parallel to the longitudinal axis in the unexpanded configuration and generally perpendicular to the longitudinal axis in the expanded configuration.

24 Claims, 26 Drawing Sheets

(51) Int. Cl.
*A61B 19/00* (2006.01)
*A61B 17/00* (2006.01)

(56) References Cited

U.S. PATENT DOCUMENTS

| | | | |
|---|---|---|---|
| 4,517,979 A | 5/1985 | Pecenka | |
| 4,545,367 A | 10/1985 | Tucci | |
| 6,699,247 B2* | 3/2004 | Zucherman et al. | 606/86 A |
| 7,410,501 B2 | 8/2008 | Michelson | |
| 7,931,674 B2 | 4/2011 | Zucherman et al. | |
| 7,959,652 B2 | 6/2011 | Zucherman et al. | |
| 7,985,246 B2 | 7/2011 | Trieu | |
| 7,998,174 B2* | 8/2011 | Malandain et al. | 606/249 |
| 8,007,521 B2* | 8/2011 | Malandain et al. | 606/279 |
| 8,021,393 B2 | 9/2011 | Seifert et al. | |
| 8,029,567 B2* | 10/2011 | Edidin et al. | 623/17.11 |
| 8,034,080 B2* | 10/2011 | Malandain et al. | 606/249 |
| 8,038,698 B2* | 10/2011 | Edidin et al. | 606/246 |
| 8,043,335 B2* | 10/2011 | Malandain et al. | 606/249 |
| 8,075,593 B2 | 12/2011 | Hess | |
| 8,105,358 B2 | 1/2012 | Phan | |
| 8,109,972 B2 | 2/2012 | Zucherman et al. | |
| 8,123,807 B2* | 2/2012 | Kim | 623/17.12 |
| 8,142,479 B2 | 3/2012 | Hess | |
| 8,147,516 B2* | 4/2012 | Malandain et al. | 606/246 |
| 8,167,944 B2* | 5/2012 | Kim | 623/17.11 |
| 8,172,878 B2 | 5/2012 | Yue | |
| 8,192,466 B2 | 6/2012 | Yue et al. | |
| 8,216,278 B2 | 7/2012 | Gabelberger et al. | |
| 8,221,458 B2* | 7/2012 | Malandain et al. | 606/246 |
| 8,221,462 B2 | 7/2012 | Dwyer et al. | |
| 8,231,656 B2 | 7/2012 | Lee et al. | |
| 8,246,655 B2 | 8/2012 | Jackson et al. | |
| 8,267,970 B2 | 9/2012 | Serhan et al. | |
| 8,273,108 B2 | 9/2012 | Altarac et al. | |
| 8,277,488 B2 | 10/2012 | Altarac et al. | |
| 8,317,864 B2* | 11/2012 | Kim | 623/17.11 |
| 2003/0195628 A1 | 10/2003 | Bao et al. | 623/17.12 |
| 2003/0220649 A1* | 11/2003 | Bao et al. | 606/90 |
| 2004/0098017 A1* | 5/2004 | Saab et al. | 606/192 |
| 2004/0260397 A1* | 12/2004 | Lambrecht et al. | 623/17.16 |
| 2005/0113928 A1* | 5/2005 | Cragg et al. | 623/17.16 |
| 2005/0245937 A1 | 11/2005 | Winslow | |
| 2005/0261768 A1 | 11/2005 | Trieu | |
| 2006/0084983 A1* | 4/2006 | Kim | 606/61 |
| 2006/0084985 A1* | 4/2006 | Kim | 606/61 |
| 2006/0084988 A1 | 4/2006 | Kim | |
| 2006/0149380 A1* | 7/2006 | Lotz et al. | 623/17.12 |
| 2006/0264938 A1 | 11/2006 | Zucherman | |
| 2006/0264939 A1 | 11/2006 | Zucherman | |
| 2006/0271049 A1 | 11/2006 | Zucherman | |
| 2007/0010813 A1 | 1/2007 | Zucherman | |
| 2007/0032790 A1 | 2/2007 | Aschmann et al. | |
| 2007/0142915 A1* | 6/2007 | Altarac et al. | 623/17.11 |
| 2007/0161991 A1* | 7/2007 | Altarac et al. | 606/61 |
| 2007/0225807 A1 | 9/2007 | Phan et al. | |
| 2007/0233076 A1 | 10/2007 | Trieu | |
| 2007/0260245 A1 | 11/2007 | Malandain et al. | |
| 2007/0265623 A1* | 11/2007 | Malandain et al. | 606/61 |
| 2007/0270823 A1* | 11/2007 | Trieu et al. | 606/61 |
| 2007/0276372 A1 | 11/2007 | Malandain et al. | |
| 2007/0276373 A1* | 11/2007 | Malandain | 606/61 |
| 2007/0276493 A1 | 11/2007 | Malandain et al. | |
| 2007/0276497 A1* | 11/2007 | Anderson | 623/17.12 |
| 2007/0282340 A1 | 12/2007 | Malandain | |
| 2007/0282442 A1 | 12/2007 | Malandain et al. | |
| 2007/0299526 A1* | 12/2007 | Malandain | 623/17.16 |
| 2008/0039944 A1* | 2/2008 | Malandain et al. | 623/17.16 |
| 2008/0051891 A1* | 2/2008 | Malandain et al. | 623/17.11 |
| 2008/0051892 A1* | 2/2008 | Malandain et al. | 623/17.11 |
| 2008/0051893 A1* | 2/2008 | Malandain et al. | 623/17.11 |
| 2008/0051894 A1* | 2/2008 | Malandain et al. | 623/17.11 |
| 2008/0058824 A1* | 3/2008 | Reiley et al. | 606/92 |
| 2008/0058934 A1* | 3/2008 | Malandain et al. | 623/17.11 |
| 2008/0058935 A1* | 3/2008 | Malandain et al. | 623/17.11 |
| 2008/0071380 A1* | 3/2008 | Sweeney | 623/17.16 |
| 2008/0082167 A1* | 4/2008 | Edidin et al. | 623/17.11 |
| 2008/0108990 A1 | 5/2008 | Mitchell et al. | |
| 2008/0147192 A1* | 6/2008 | Edidin et al. | 623/17.16 |
| 2008/0167657 A1* | 7/2008 | Greenhalgh | 606/90 |
| 2008/0177306 A1* | 7/2008 | Lamborne et al. | 606/246 |
| 2008/0177308 A1* | 7/2008 | McLeer | 606/247 |
| 2008/0177309 A1* | 7/2008 | McLeer | 606/247 |
| 2008/0195152 A1 | 8/2008 | Altarac et al. | |
| 2008/0221685 A9* | 9/2008 | Altarac et al. | 623/17.11 |
| 2008/0287997 A1 | 11/2008 | Altarac et al. | |
| 2008/0319550 A1 | 12/2008 | Altarac et al. | |
| 2009/0118833 A1* | 5/2009 | Hudgins et al. | 623/17.16 |
| 2009/0138046 A1 | 5/2009 | Altarac et al. | |
| 2009/0138055 A1 | 5/2009 | Altarac et al. | |
| 2009/0234389 A1 | 9/2009 | Chuang et al. | |
| 2009/0281628 A1* | 11/2009 | Oglaza et al. | 623/17.15 |
| 2009/0292316 A1 | 11/2009 | Hess | |
| 2009/0299374 A1* | 12/2009 | Tilson et al. | 606/94 |
| 2009/0299401 A1* | 12/2009 | Tilson | 606/192 |
| 2009/0301643 A1* | 12/2009 | Tilson et al. | 156/155 |
| 2009/0306589 A1* | 12/2009 | Tilson et al. | 604/103.1 |
| 2009/0326581 A1* | 12/2009 | Galley et al. | 606/249 |
| 2010/0057130 A1 | 3/2010 | Yue | |
| 2010/0106191 A1* | 4/2010 | Yue et al. | 606/249 |
| 2010/0152654 A1* | 6/2010 | Tilson et al. | 604/103.06 |
| 2010/0152775 A1 | 6/2010 | Seifert et al. | |
| 2010/0222816 A1 | 9/2010 | Gabelberger et al. | |
| 2010/0222817 A1 | 9/2010 | Perez-Cruet et al. | |
| 2010/0228272 A1* | 9/2010 | Balbierz et al. | 606/153 |
| 2010/0234889 A1 | 9/2010 | Hess | |
| 2010/0241152 A1* | 9/2010 | Tilson et al. | 606/191 |
| 2010/0241153 A1* | 9/2010 | Tilson et al. | 606/191 |
| 2010/0241178 A1* | 9/2010 | Tilson et al. | 606/86 R |
| 2010/0249775 A1* | 9/2010 | Gaiser et al. | 606/41 |
| 2010/0262240 A1* | 10/2010 | Chavatte et al. | 623/17.11 |
| 2010/0305611 A1 | 12/2010 | Zucherman et al. | |
| 2011/0046674 A1 | 2/2011 | Calvosa et al. | |
| 2011/0054531 A1 | 3/2011 | Lamborne et al. | |
| 2011/0071568 A1 | 3/2011 | Ginn et al. | |
| 2011/0077686 A1 | 3/2011 | Mishra et al. | |
| 2011/0144697 A1* | 6/2011 | Malandain et al. | 606/279 |
| 2011/0160773 A1 | 6/2011 | Aschmann et al. | |
| 2011/0172710 A1* | 7/2011 | Thommen et al. | 606/249 |
| 2011/0179573 A1* | 7/2011 | North et al. | 5/632 |
| 2011/0190816 A1 | 8/2011 | Sheffer et al. | |
| 2011/0190817 A1* | 8/2011 | Thommen et al. | 606/249 |
| 2011/0198019 A1* | 8/2011 | Tilson et al. | 156/155 |
| 2011/0313458 A1 | 12/2011 | Butler et al. | |
| 2012/0004729 A1* | 1/2012 | Zipnick | 623/17.16 |
| 2012/0029565 A1 | 2/2012 | Seifert et al. | |
| 2012/0078301 A1 | 3/2012 | Hess | |
| 2012/0089185 A1 | 4/2012 | Gabelberger | |
| 2012/0136393 A1* | 5/2012 | Auyoung | 606/249 |
| 2012/0150229 A1 | 6/2012 | Hess | |
| 2012/0209164 A1* | 8/2012 | Kagan et al. | 604/8 |
| 2012/0296378 A1 | 11/2012 | Lee et al. | |
| 2013/0012998 A1* | 1/2013 | Altarac et al. | 606/279 |
| 2013/0165975 A1* | 6/2013 | Tebbe et al. | 606/249 |

FOREIGN PATENT DOCUMENTS

| | | |
|---|---|---|
| WO | 2005115261 A1 | 12/2005 |
| WO | 2008011378 A1 | 1/2008 |
| WO | 2008/088613 | 7/2008 |

OTHER PUBLICATIONS

International Search Report for International Application No. PCT/US2010/055572, dated Apr. 19, 2011 (7 pages).

* cited by examiner

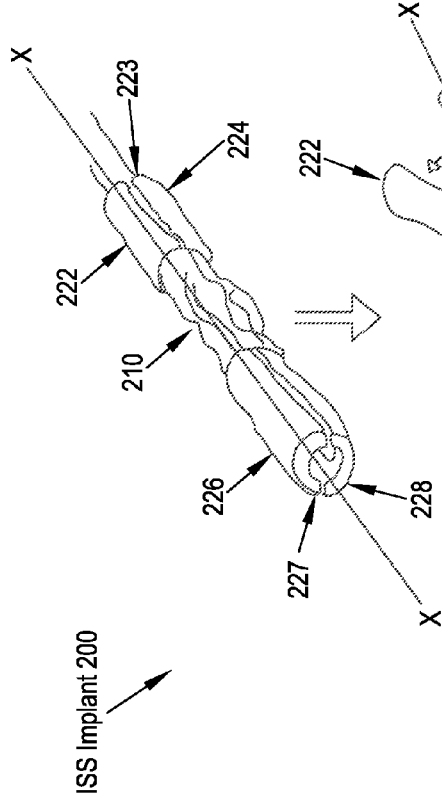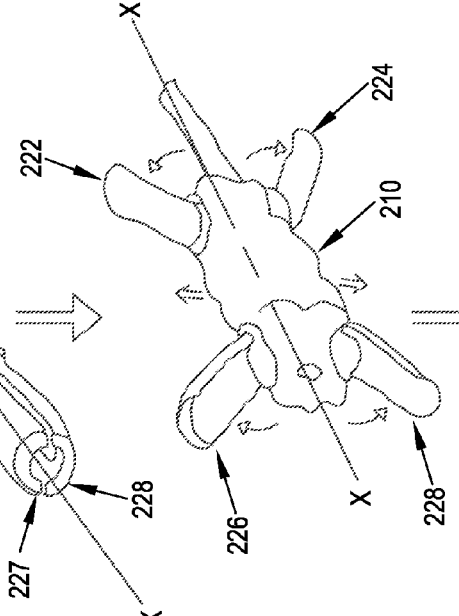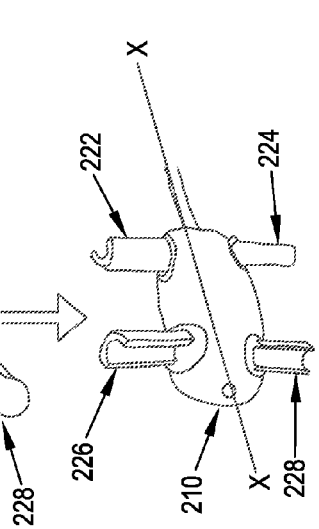

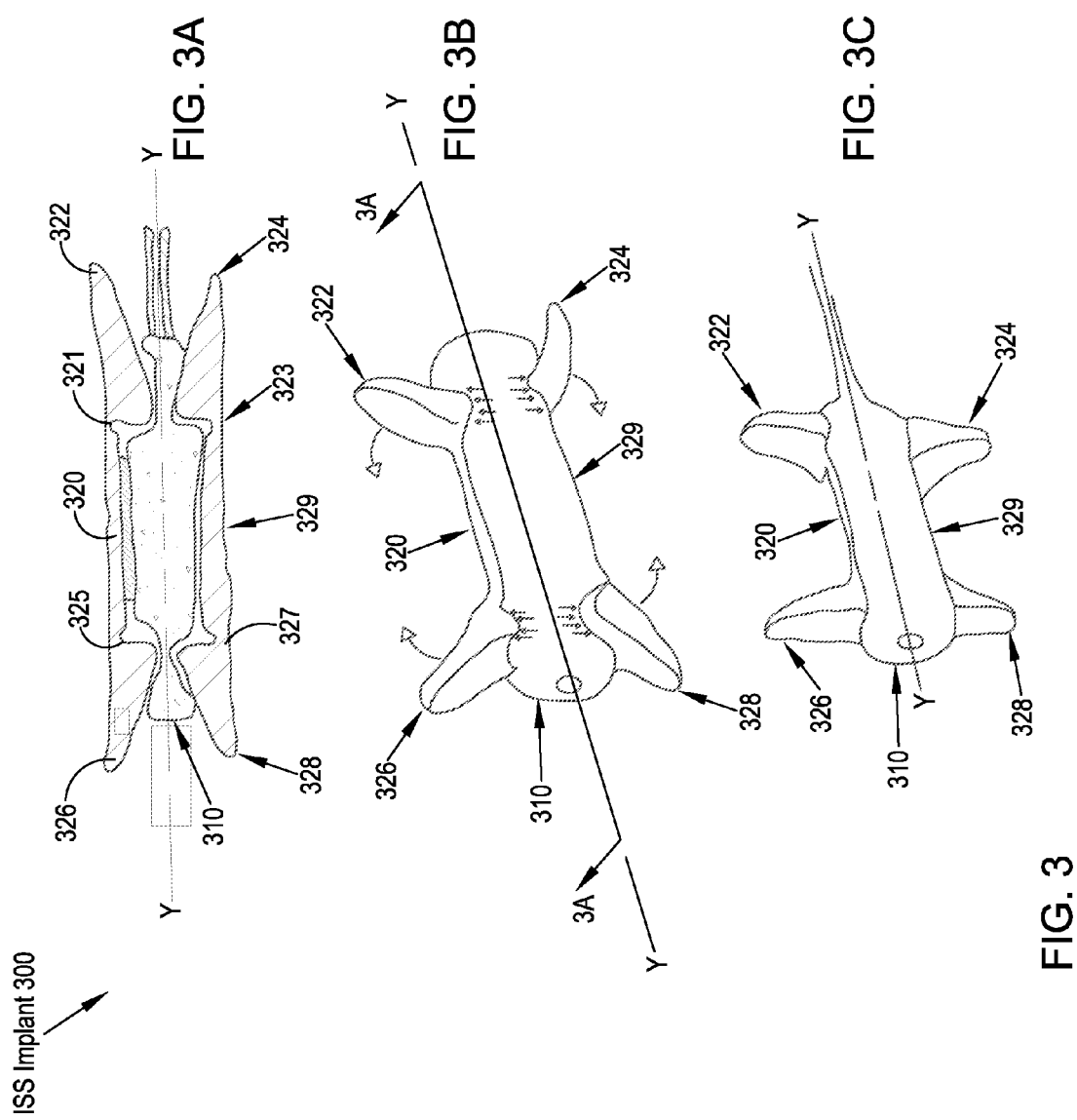

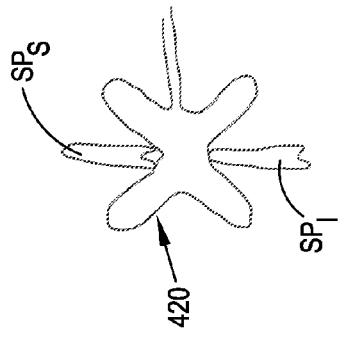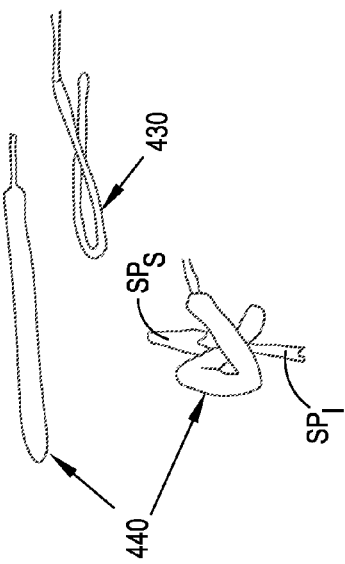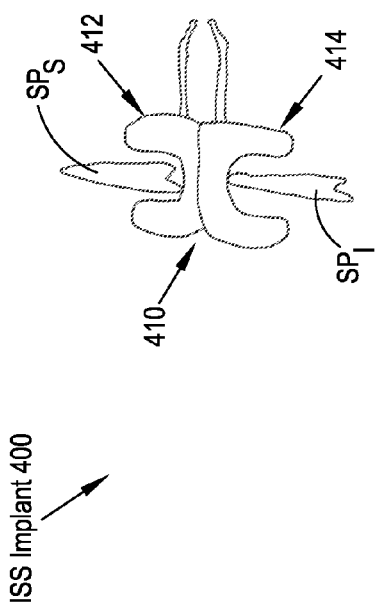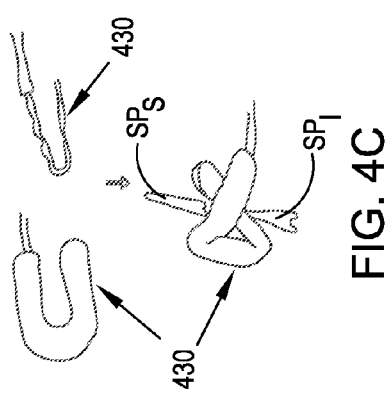
FIG. 4

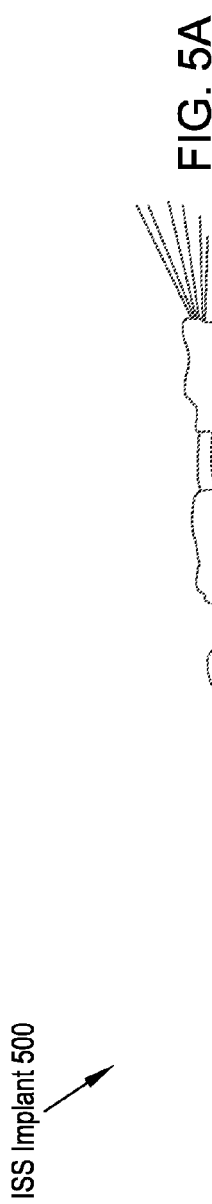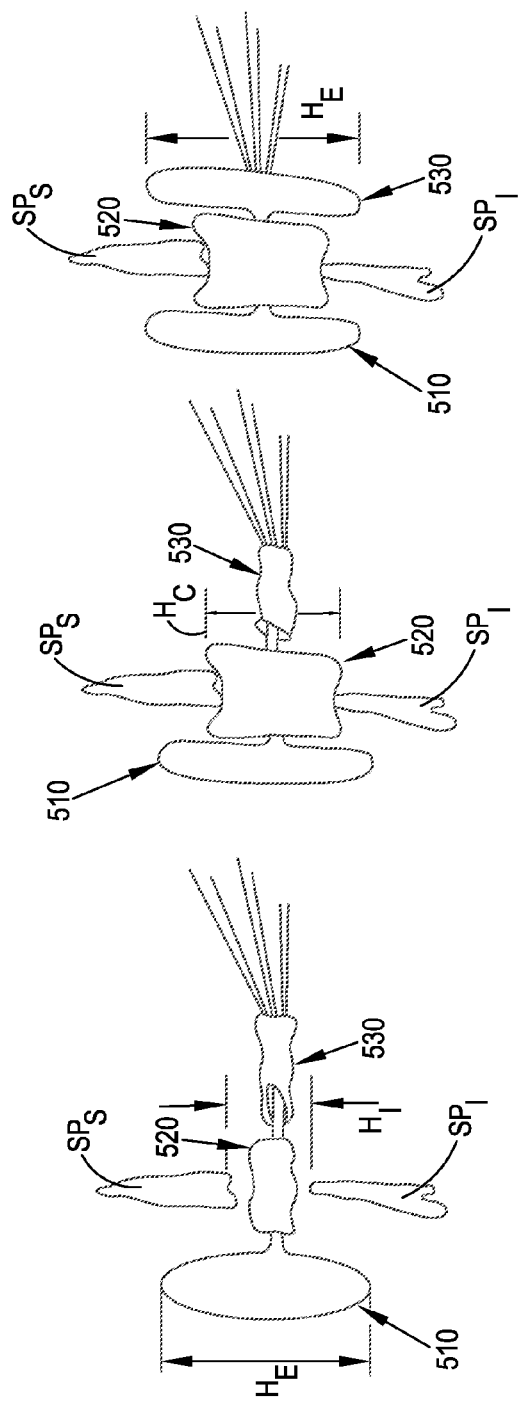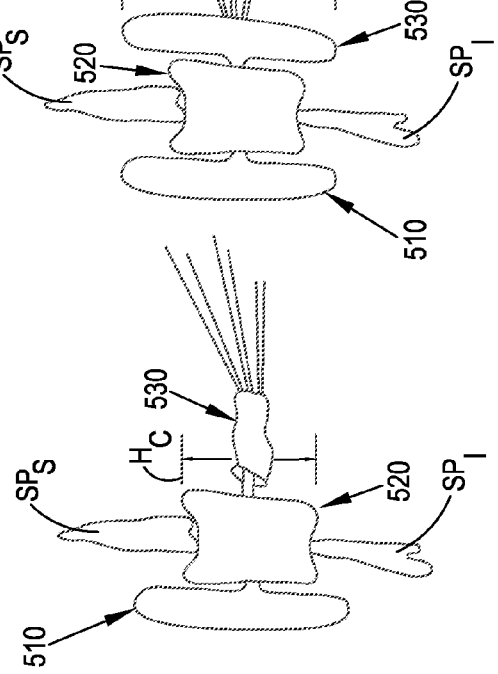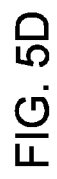
FIG. 5A  FIG. 5B  FIG. 5C  FIG. 5D  FIG. 5

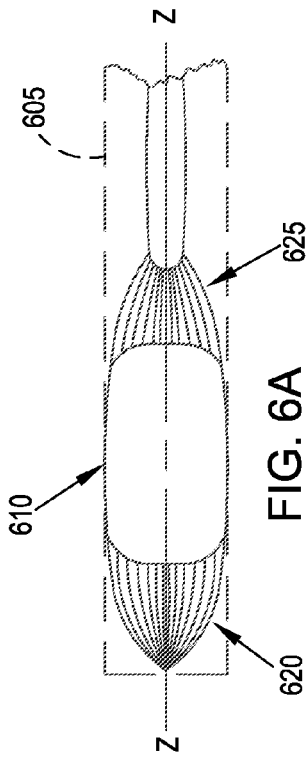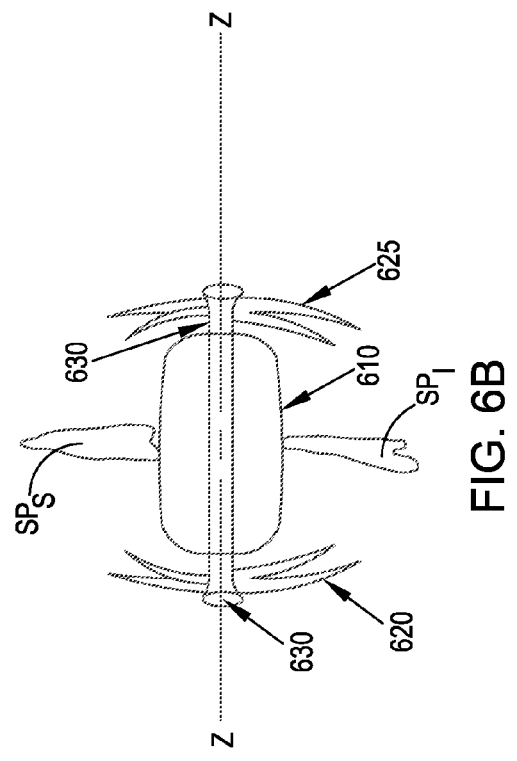
FIG. 6A  FIG. 6B
FIG. 6

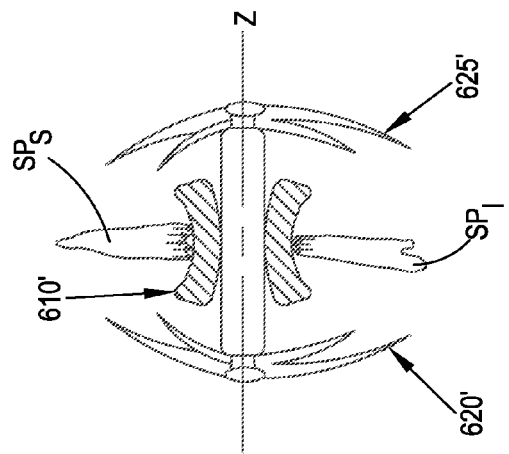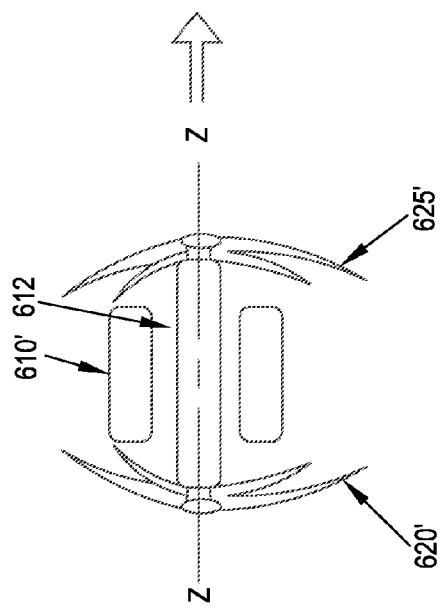
FIG. 7A  FIG. 7B
FIG. 7

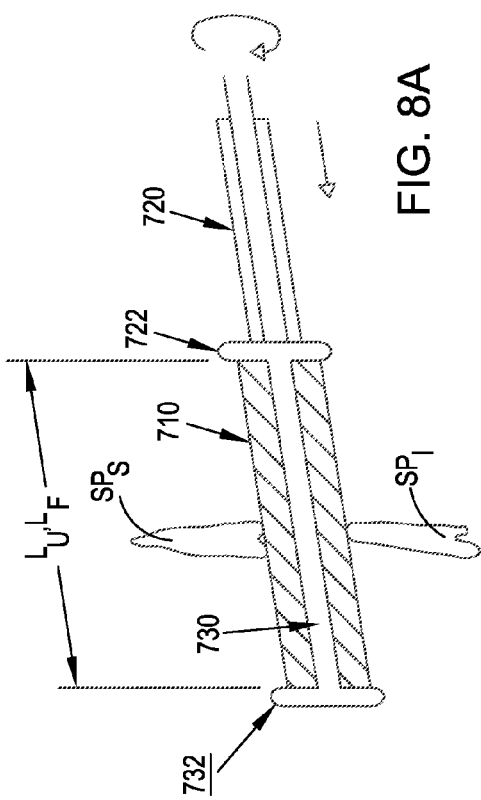
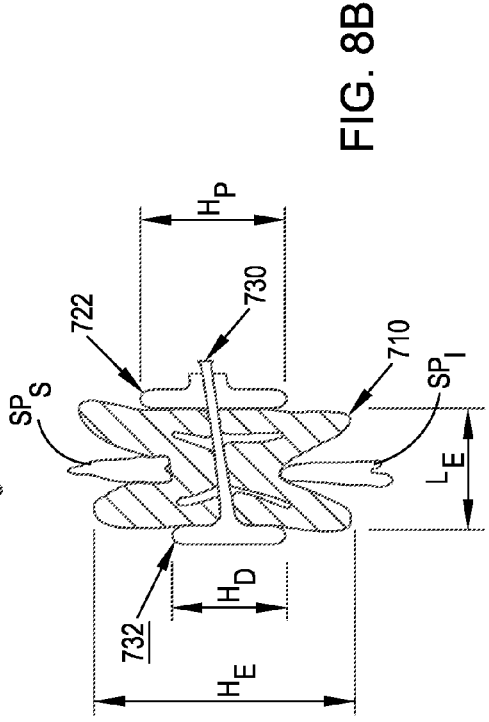
FIG. 8A
FIG. 8B
FIG. 8

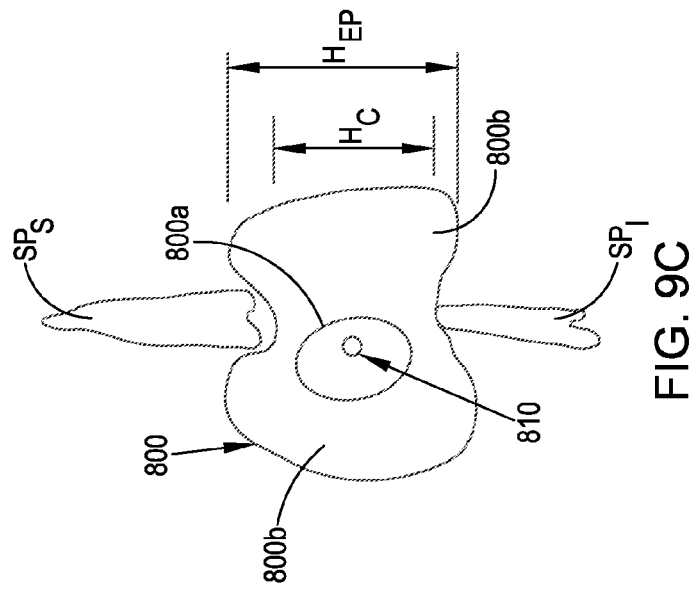
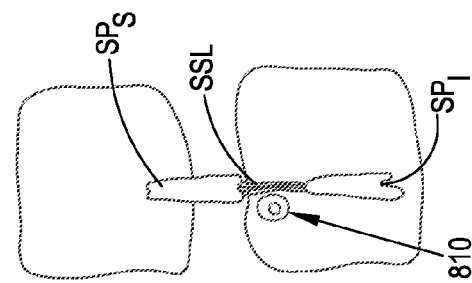
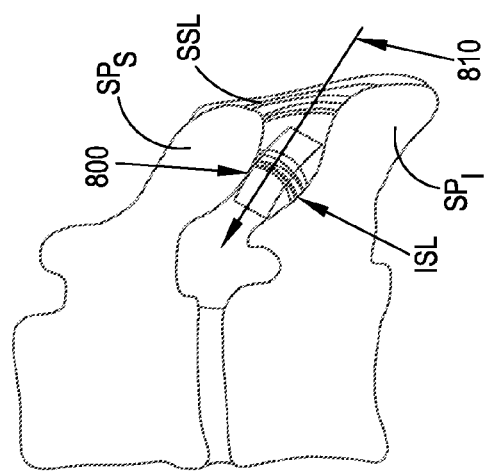
FIG. 9

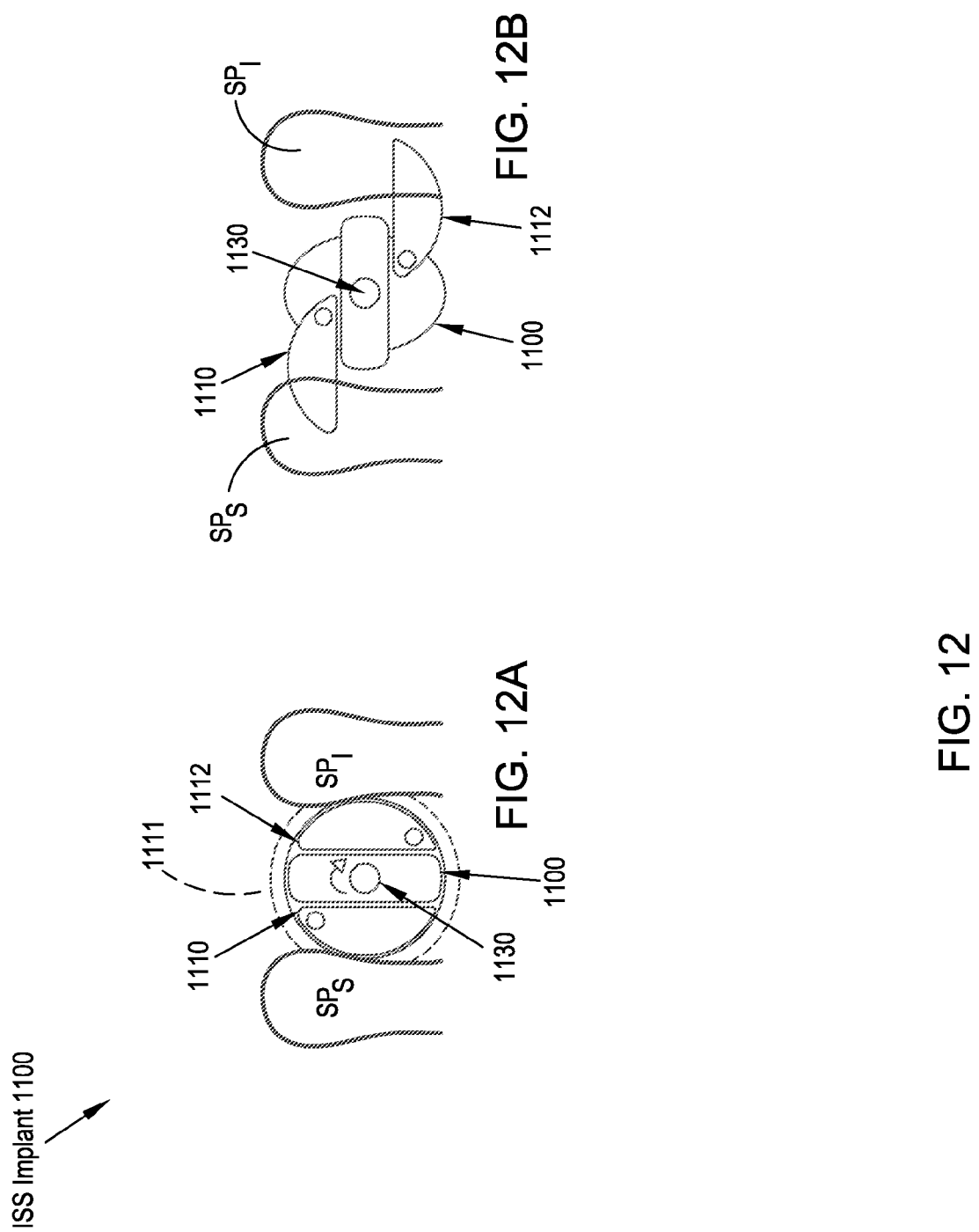

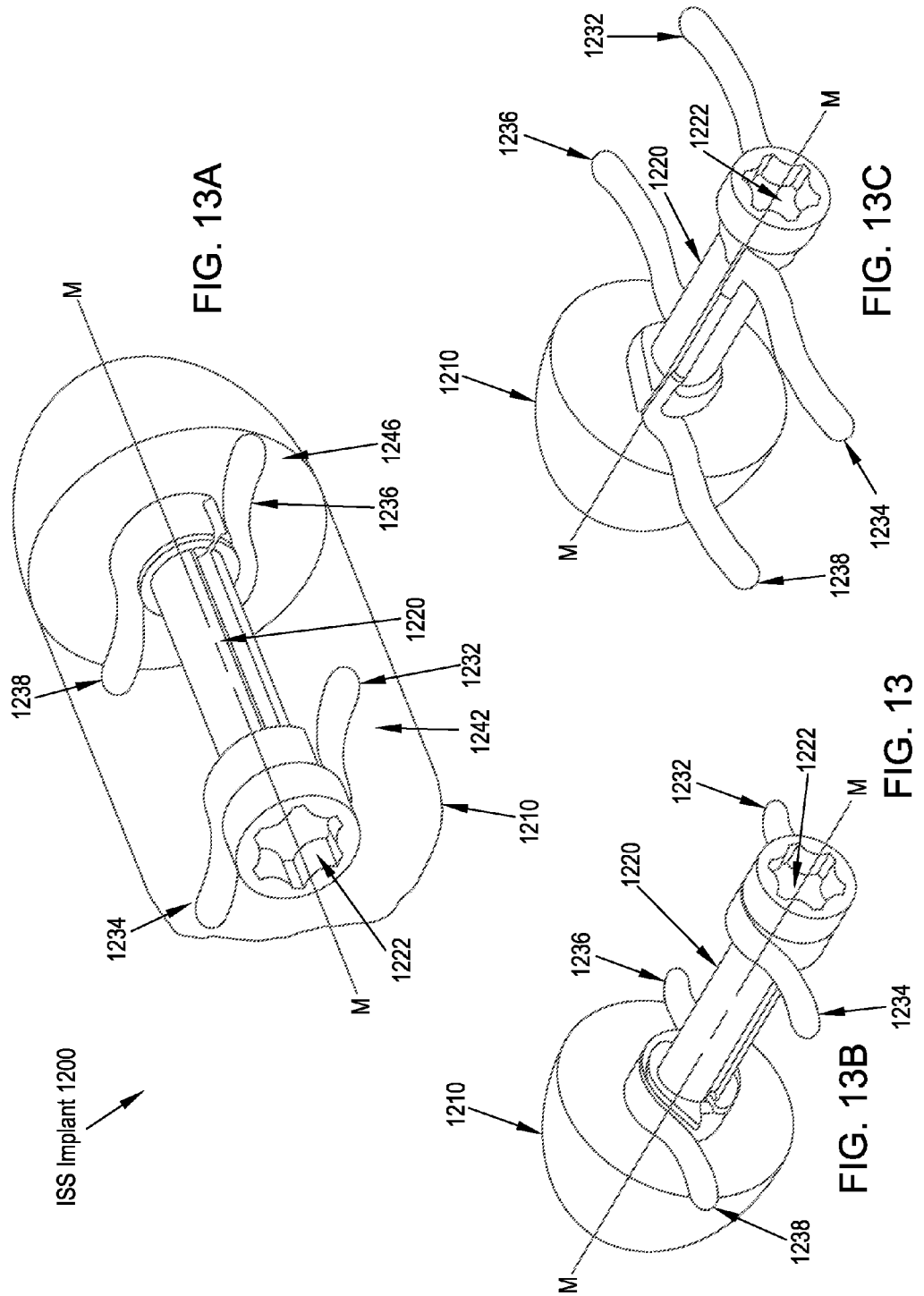

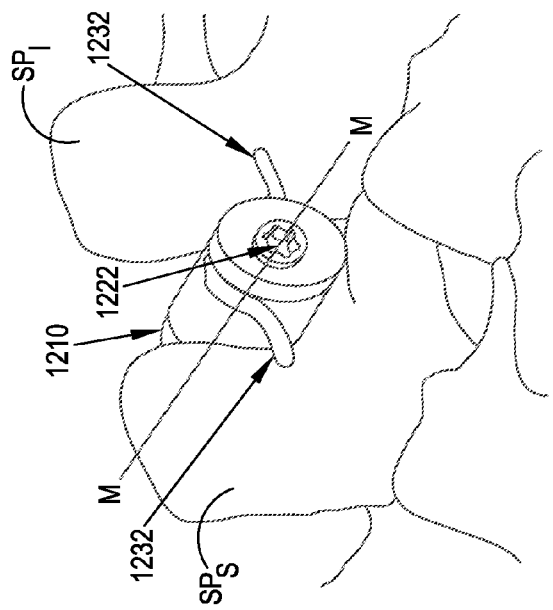
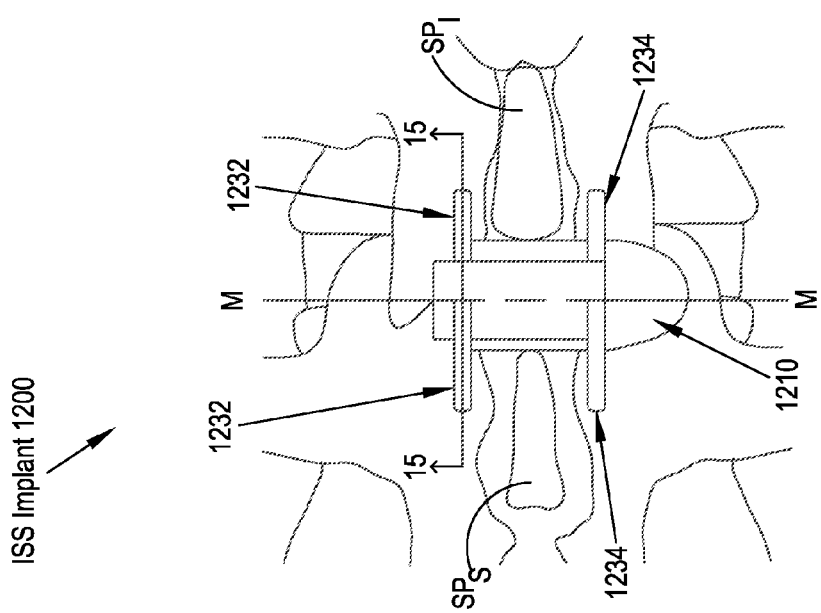
FIG. 14B
FIG. 14A
FIG. 14

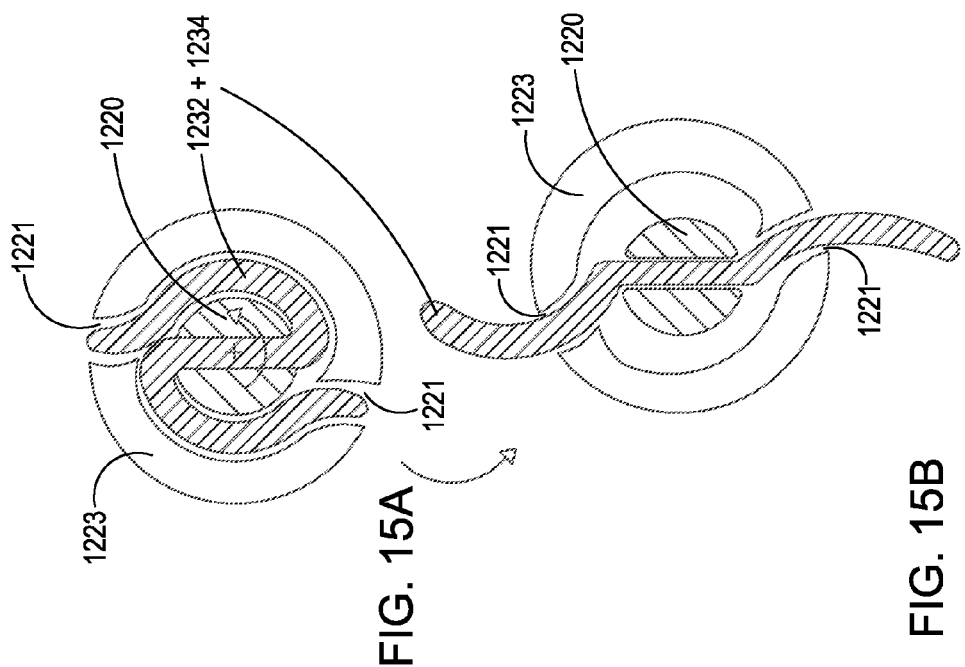
FIG. 15A
FIG. 15B
FIG. 15

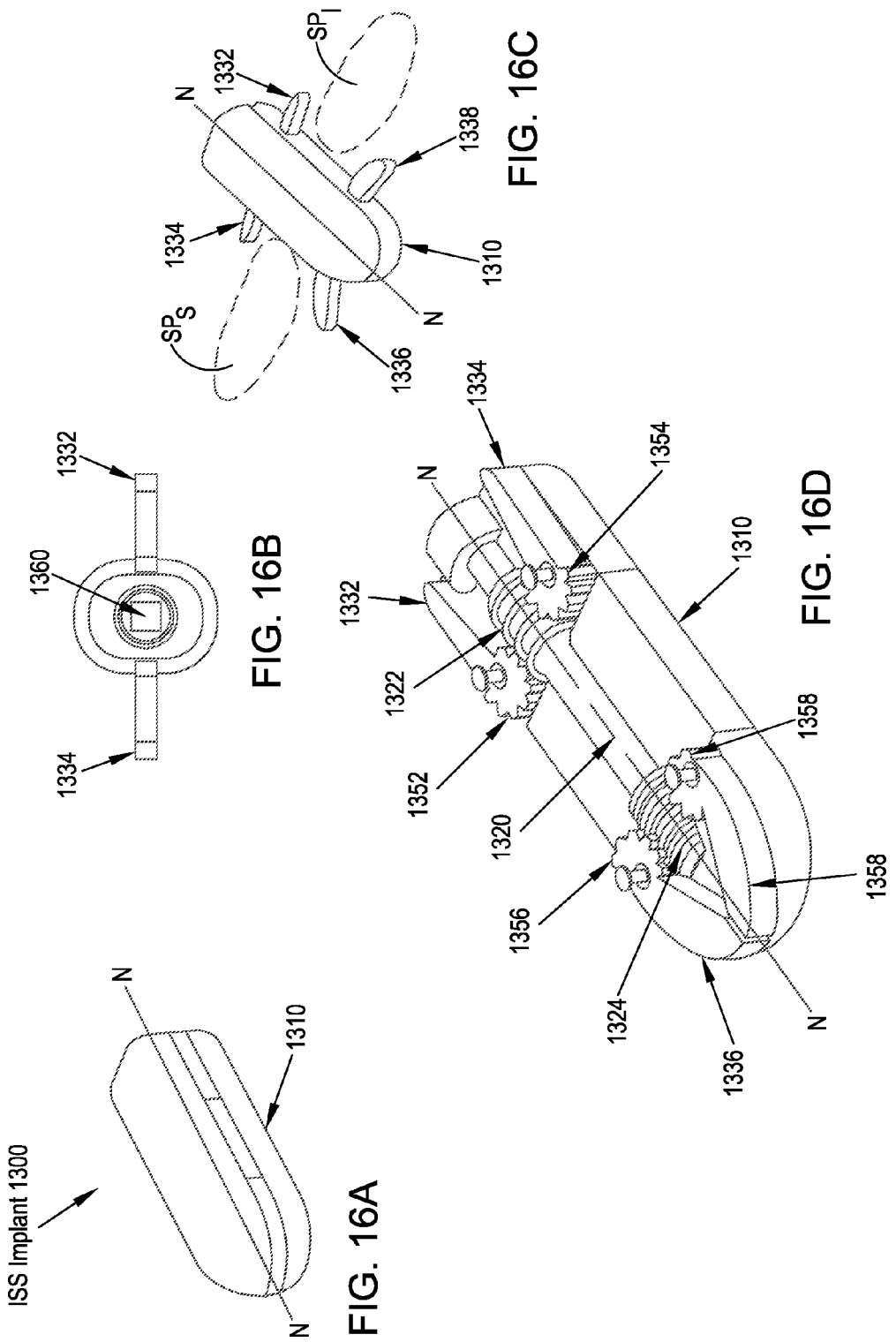

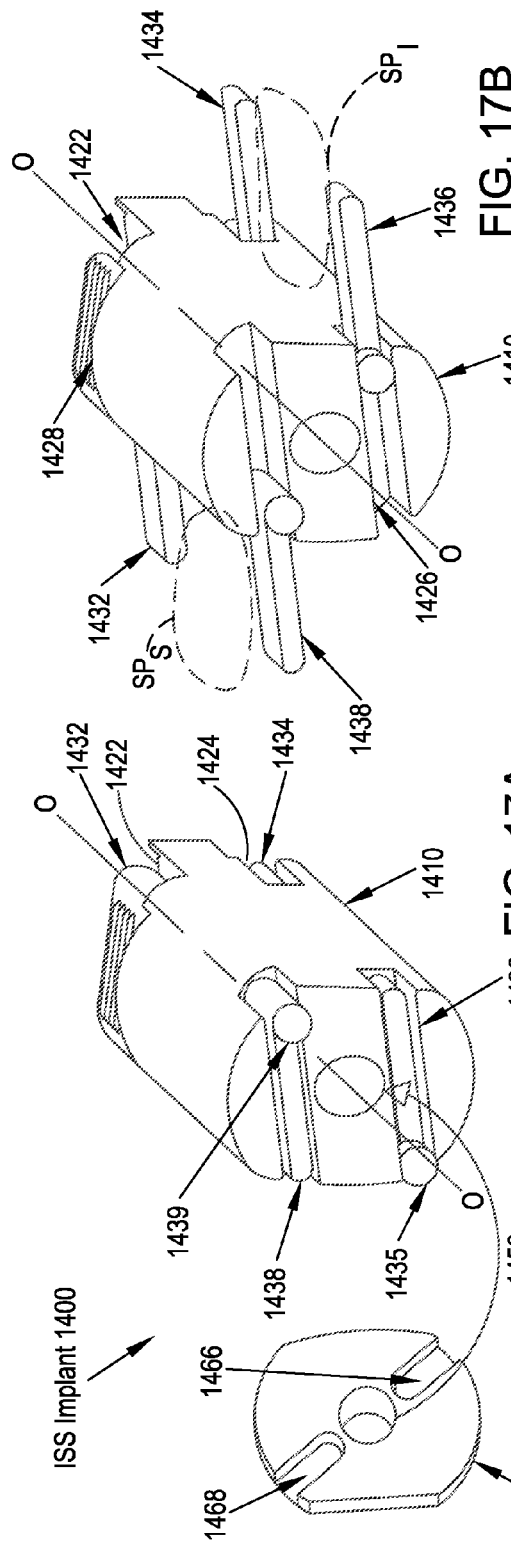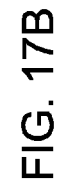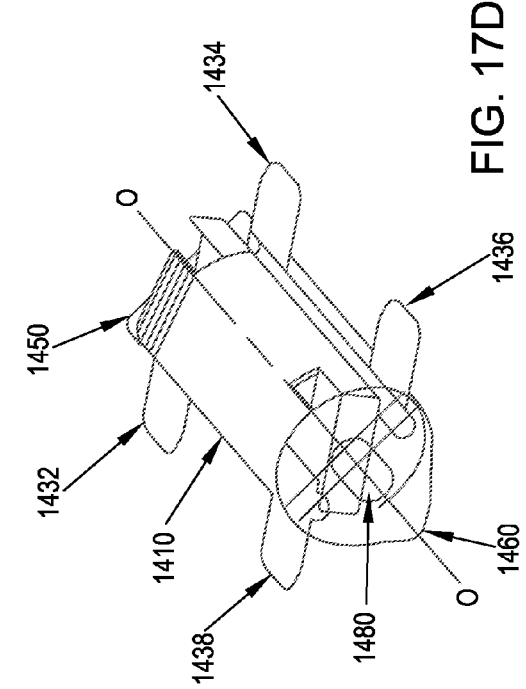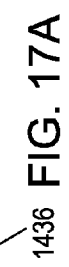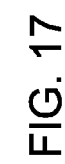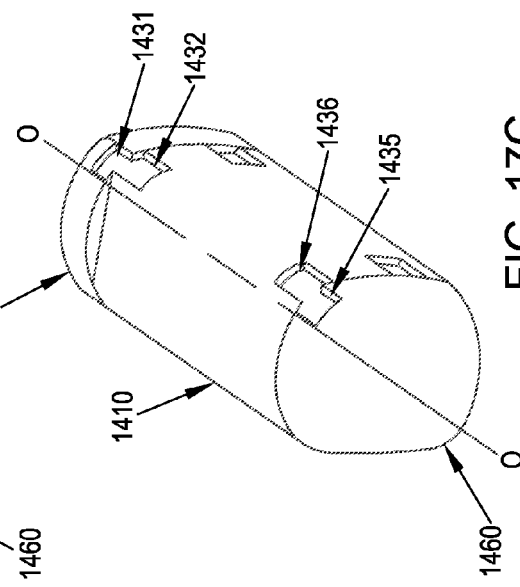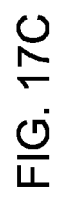

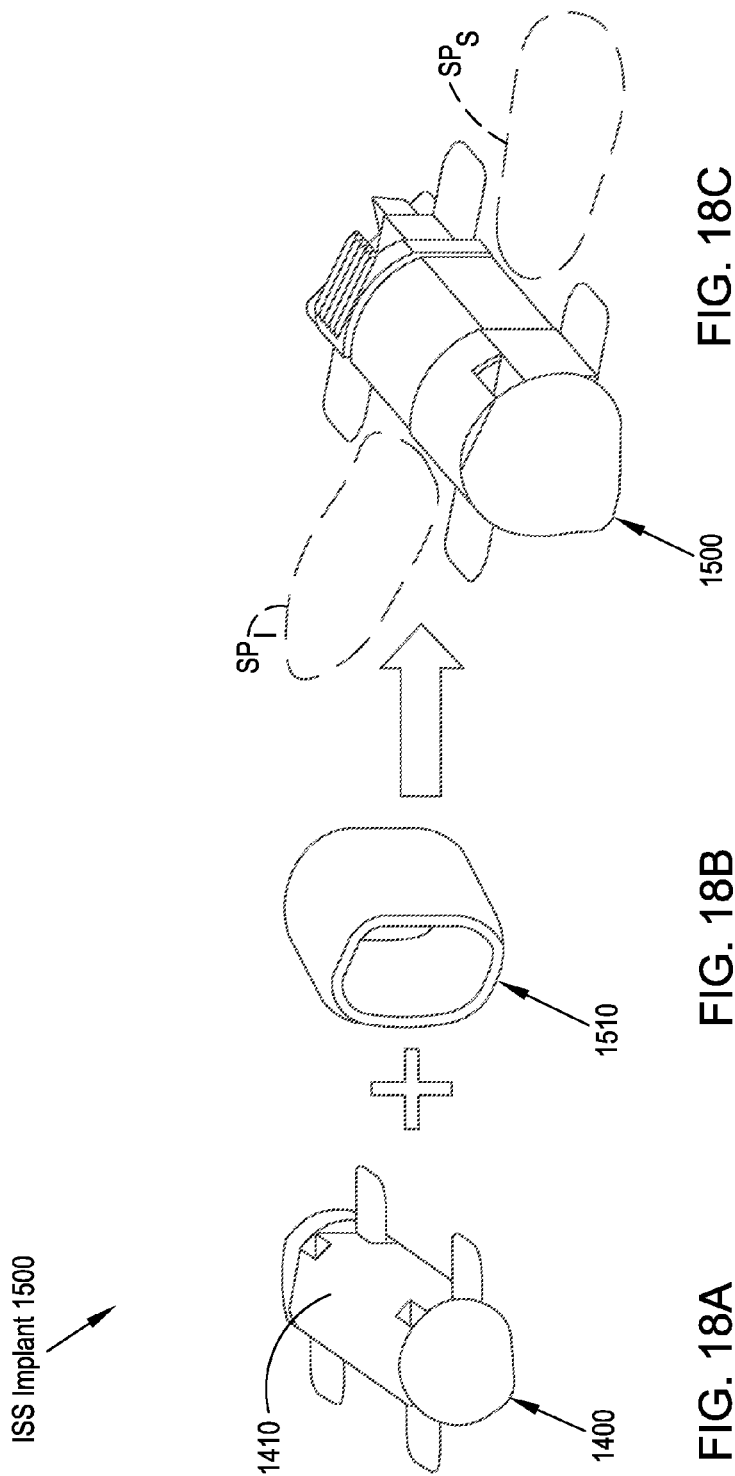

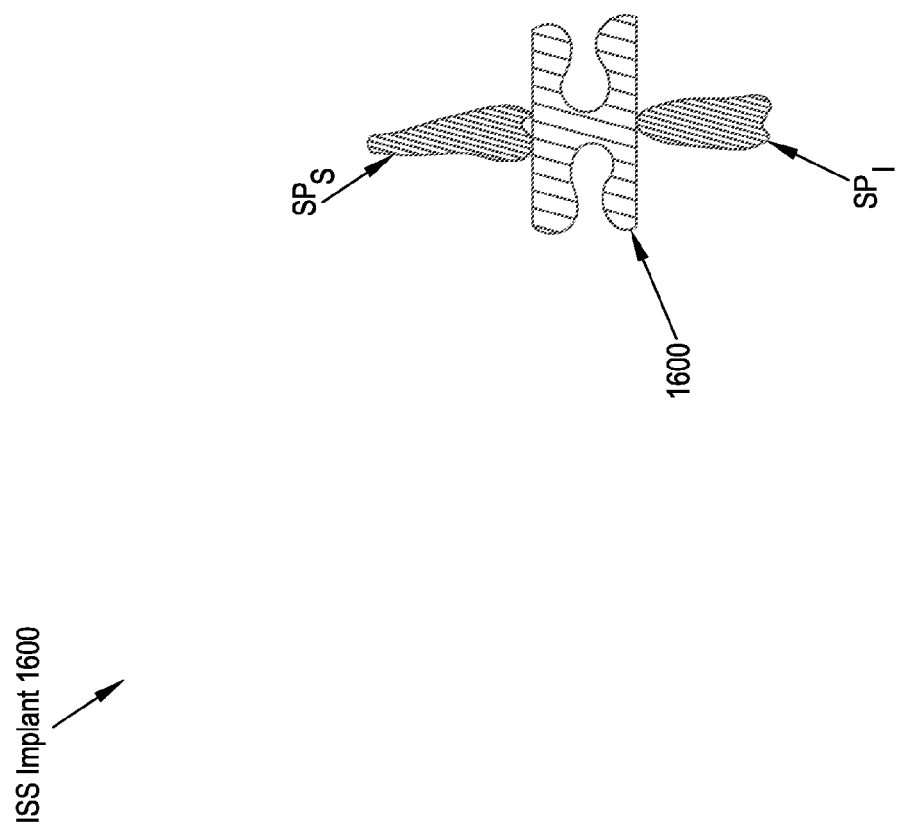

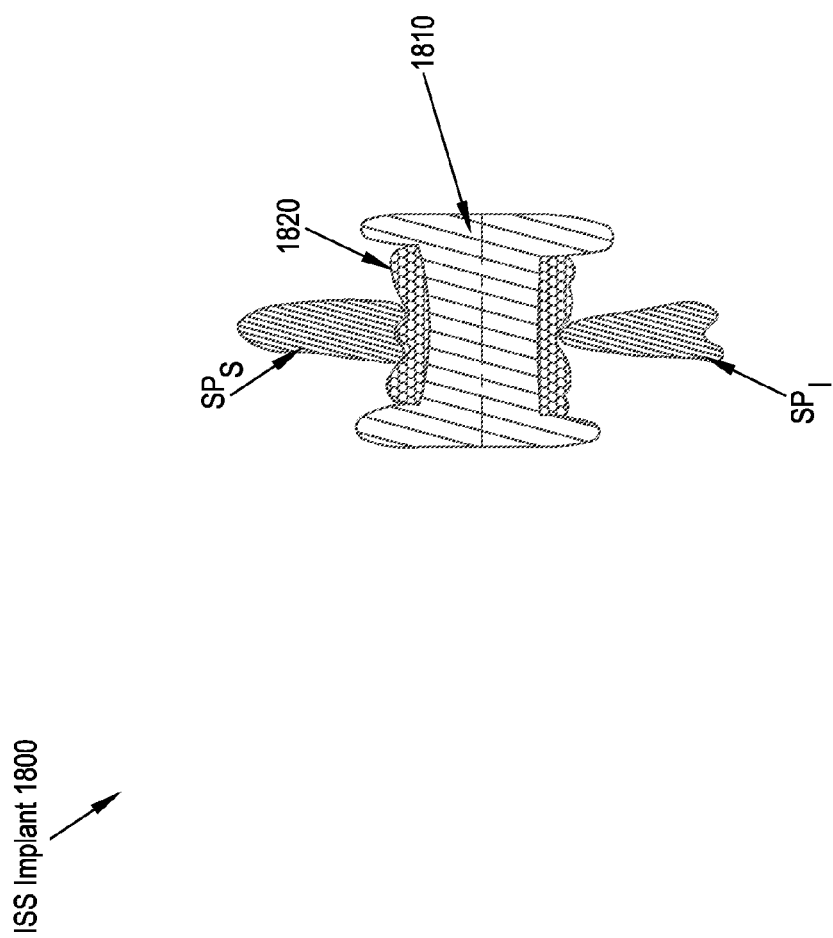

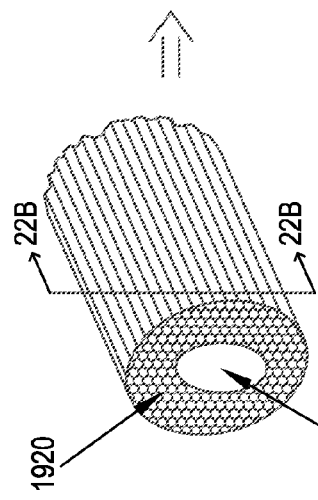
FIG. 22A
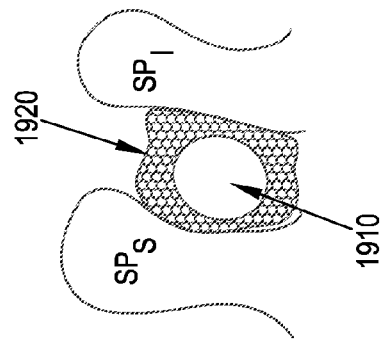
FIG. 22B
FIG. 22

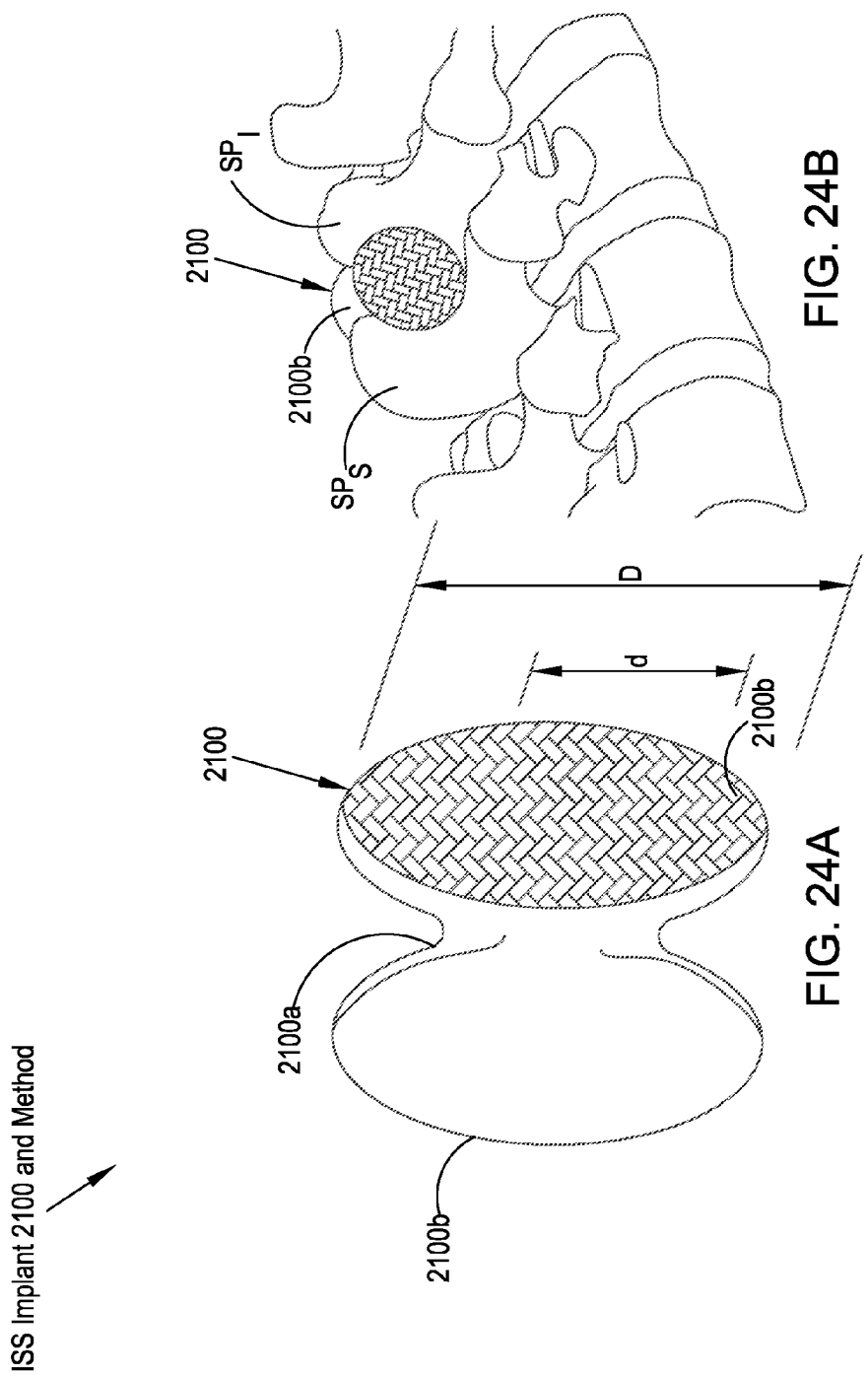

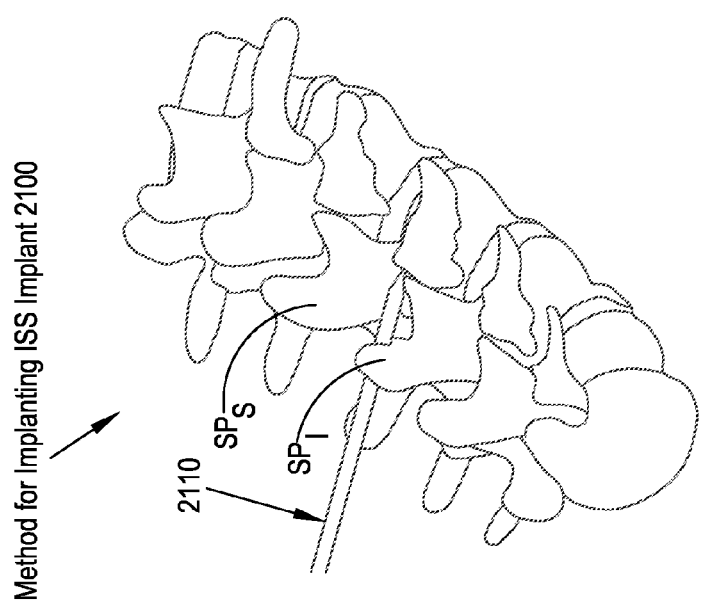
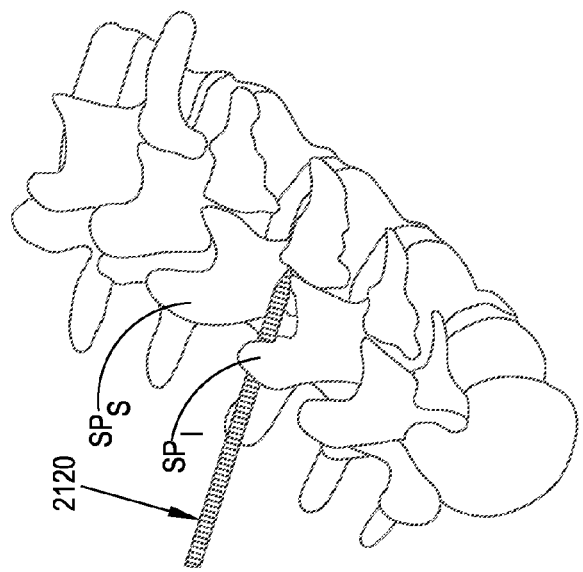
FIG. 25A
FIG. 25B
FIG. 25

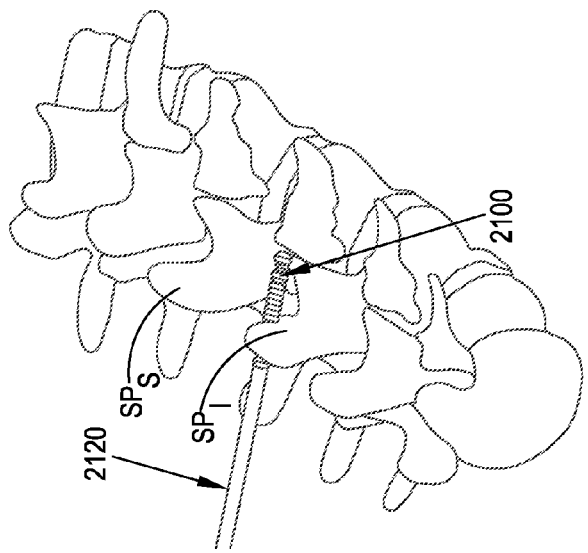
FIG. 26B
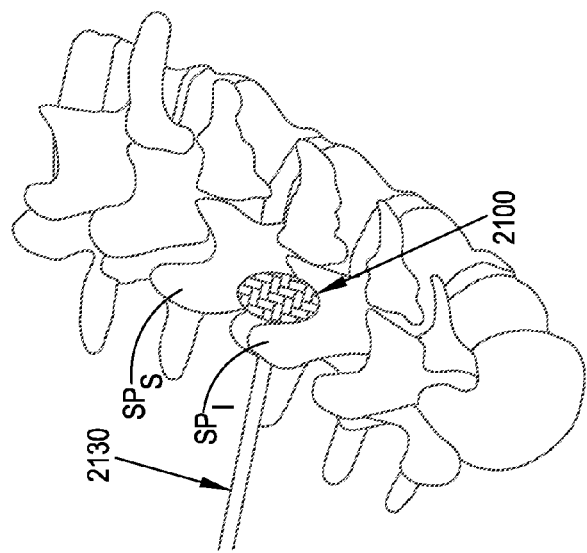
FIG. 26A
FIG. 26

MINIMALLY INVASIVE INTERSPINOUS PROCESS SPACER IMPLANTS AND METHODS

CROSS-REFERENCE TO RELATED APPLICATION

This application claims priority to U.S. Patent Application No. 61/258,632, filed Nov. 6, 2009, and entitled "Minimally Invasive Interspinous Process Spacer Implants and Methods," which is incorporated herein by reference in its entirety.

BACKGROUND

A human vertebrae has a rearwardly projecting portion known as a spinous process. Bending of the spine, particularly extension of the spine, can cause the spinous processes of adjacent vertebrae to move toward each other. This constricts the space in the spinal canal and foramina and may cause pain. Such pain may be exacerbated when the spinal canal or nerve roots exiting the canal are constricted by natural degeneration of the spine, such as by spinal stenosis or degenerative disc disease. Such pain may be treated by positioning an implant in a space between adjacent spinous processes to maintain a predetermined distance between the adjacent spinous processes, thereby providing a minimum amount of space between the spinous processes.

Generally there are two types of spinal stenosis: (1) hard or rigid spinal stenosis or (2) soft or dynamic spinal stenosis. In both cases, spinal stenosis may be caused by excessive growth of tissue due to degeneration, loss of disc height, excessive load in a particular area of the spine as well disorders such as spondilolisthesis where the normal relative position and/or orientation of the adjacent vertebrae have been modified.

A difference between the two types of spinal stenosis is that, generally, dynamic spinal stenosis may be treated with distraction of the vertebra at the affected level while hard stenosis generally requires removal of the tissue that obstructs the spinal canal or foramina at the affected level. In the case of tissue removal, the surgical treatment typically results in some loss of stability to the spine. Therefore, it is preferable to increase the stability of the spinal segment by inserting an interspinous process spacer ("ISS") between the spinous processes of the adjacent vertebrae to increase the stiffness of the segment and/or to restrict motion of that segment.

Some current implants are made of separate pieces that require insertion from both sides of the spinous processes using a posterior approach that necessitates rather wide openings into a patient, cutting both left and right thoracolumbar fascia, as well as stripping the multifidus muscles from their attachments. It is desirable to provide an implant for insertion between the spinous processes of adjacent vertebrae which are inserted through a single opening in a minimal invasive approach and may be held firmly in position between the vertebrae. It is desirable for the surgical incision and surgical pathway to extend laterally into the space between the adjacent spinous processes, thereby preserving major ligaments and musculature of the spine at the impacted level.

SUMMARY

The present disclosure relates generally to orthopedics. More specifically, the present disclosure relates to implants and methods for interspinous process spacing using a minimally invasive surgical technique, preferably using a preferred Interspinous Process Spacer ("ISS").

In accordance with some implementations, there is provided an interspinous process spacer for implantation in an interspinous space between a superior spinous process and an inferior spinous process. The interspinous process spacer may include a balloon-like body having a distal end, a proximal end, and a longitudinal axis extending between the proximal and distal ends, the balloon-like body being arrangeable in an unexpanded configuration and an expanded configuration. The interspinous process spacer may further include a first deployable protrusion mounted proximate the proximal end and a second deployable protrusion mounted proximate the distal end. The first and second deployable protrusions may be oriented generally parallel to the longitudinal axis in the unexpanded configuration and generally perpendicular to the longitudinal axis in the expanded configuration.

In accordance with other implementations, an interspinous process spacer for implantation in an interspinous space between a superior spinous process and an inferior spinous process is provided. The interspinous process spacer may include a symmetrical pre-shaped balloon-like body having a distal end, a proximal end, and a longitudinal axis extending between the proximal and distal ends, the balloon-like body being arrangeable in an unexpanded configuration and an expanded configuration.

In accordance with yet other implementations, there is provided an interspinous process spacer for implantation in an interspinous space between a superior spinous process and an inferior spinous process. The interspinous process spacer may include a central generally rigid rod member having a distal end, a proximal end, and a longitudinal axis extending between the proximal and distal ends, the generally rigid rod member being arrangeable in an unexpanded configuration and an expanded configuration. The interspinous process spacer may include an inflatable spacer portion disposed about the longitudinal axis, a first plurality of wires disposed axially about the proximal end, and a second plurality of wires disposed axially about the distal end. The first and second plurality of wires may be oriented generally parallel to the longitudinal axis in the unexpanded configuration and generally perpendicular to the longitudinal axis in the expanded configuration.

In accordance with further implementations, a method of implanting an inflatable interspinous process spacer having deployable securing elements into an interspinous space between a superior spinous process and an inferior spinous process is described. The method may include inserting a guiding device into an interspinous ligament in the interspinous space, introducing the process spacer via the guiding device into the interspinous space, inflating the process spacer such that a first portion of the process spacer is positioned contralaterally of the interspinous space and a second portion of the process spacer is positioned ipsilaterally of the interspinous space, and deploying the deployable securing elements.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF THE DRAWINGS

The foregoing summary, as well as the following detailed description of preferred embodiments of the instrument, implant and method of the present application, will be better understood when read in conjunction with the appended drawings. For the purposes of illustrating the interspinous process spacer ("ISS") implants, instruments and methods of the present application, there are shown in the drawings preferred embodiments. It should be understood, however, that the application is not limited to the precise arrangements and instrumentalities shown. In the drawings:

FIGS. 2A-2C illustrate top perspective views of an ISS implant in accordance with a second preferred embodiment of the present disclosure in an unexpanded, partially expanded, and fully expanded configuration, respectively;

FIGS. 3A-3C illustrate a cross-sectional and rear perspective views of an ISS implant in accordance with a third preferred embodiment of the present disclosure in an unexpanded (FIG. 3A), partially expanded (FIG. 3B), and fully expanded (FIG. 3C) configurations, respectively;

FIGS. 4A-4D illustrate rear elevational views of a variety of ISS implants in accordance with a fourth preferred embodiment of the present disclosure;

FIGS. 5A-5D illustrate rear elevational views of an ISS implant in accordance with a fifth preferred embodiment of the present disclosure in unexpanded, first partially expanded, second partially expanded, and fully expanded configurations, respectively;

FIGS. 6A and 6B illustrate rear elevational views of an ISS implant in accordance with a sixth preferred embodiment of the present disclosure in unexpanded and expanded configurations, respectively;

FIGS. 7A and 7B illustrate rear elevational views of an ISS implant in accordance with a seventh preferred embodiment of the present disclosure in unexpanded and expanded configurations, respectively;

FIGS. 8A and 8B illustrate rear elevational views of an ISS implant in accordance with an eighth preferred embodiment of the present disclosure in unexpanded and expanded configurations, respectively;

FIGS. 9A-9C illustrate a side elevational view of an un-inflated ISS implant in accordance with a ninth preferred embodiment of the present disclosure and a guide wire during its implantation, a rear elevational view of the positioning of the guidewire prior to the insertion of the ISS implant of FIG. 9A, and a rear elevational view of an inflated ISS implant of FIG. 9A subsequent to its implantation, respectively.

FIGS. 12A and 12B illustrate side elevational views of an ISS implant in accordance with an twelfth preferred embodiment of the present disclosure in unexpanded and expanded configurations, respectively;

FIGS. 13A-13C illustrate a rear perspective view of an ISS implant in accordance with a thirteenth preferred embodiment of the present disclosure in an unexpanded configuration, a rear perspective view of the ISS implant of FIG. 12A in an unexpanded configuration with an implant body removed for clarity, and a rear perspective view of the ISS implant of FIG. 12A in an expanded configuration with the implant body removed for clarity;

FIGS. 14A and 14B illustrate a rear elevational view and a side perspective view of an alternate embodiment of the ISS implant of FIGS. 12 and 13, in which a shaft member includes longitudinal slots that allows wing pairs 1232, 1234, 1236, 1238 to be formed as unitary elements.

FIGS. 15A and 15B illustrate lateral cross-sectional views taken along line 15-15 of FIG. 14 of the ISS implant of FIGS. 13 and 14, respectively, showing the ISS implant in an unexpanded configuration (FIG. 15A) and an expanded configuration (FIG. 15B);

FIGS. 16A-16D illustrate a front perspective view of an ISS implant in accordance with a fourteenth preferred embodiment of the present disclosure in an unexpanded configuration, a side elevational view of the ISS implant of FIG. 16A in an expanded configuration, a top perspective view of the ISS implant of FIG. 16A in an expanded configuration, and a top perspective view of the ISS implant of FIG. 16A in an unexpanded configuration with a portion of an implant body removed for clarity, respectively;

FIGS. 17A-17D illustrate a side perspective, partially exploded view of an ISS implant in accordance with a fifteenth preferred embodiment of the present disclosure in an unexpanded configuration, a side perspective view of the ISS implant of FIG. 17A in an expanded configuration with a distal turning wheel removed for clarity, a side perspective view of the ISS implant of FIG. 17A in an unexpanded configuration, and a side perspective view of the ISS implant of FIG. 17A in an expanded configuration, respectively;

FIGS. 18A-18C illustrate top perspective views of an ISS implant in accordance with a sixteenth preferred embodiment, illustrating an implant body element in an expanded configuration (FIG. 18A), a balloon-type element (FIG. 18B), and the assembled ISS implant (FIG. 18C) in an expanded configuration, respectively;

FIG. 19 illustrates a rear cross-sectional view of an ISS implant in accordance with a seventeenth preferred embodiment of the present disclosure;

FIG. 21 illustrates a rear cross-sectional view of an ISS implant in accordance with an nineteenth preferred embodiment of the present disclosure;

FIGS. 22A and 22B illustrate a side perspective view and a cross-sectional view taken along line 22B-22B of FIG. 22A of an ISS implant in accordance with a twentieth preferred embodiment of the present disclosure, respectively;

FIGS. 24A and 24B illustrate a front perspective view and a side perspective view of an ISS implant in accordance with a twenty-second preferred embodiment of the present disclosure in an expanded configuration, respectively;

FIGS. 25A and 25B illustrates top perspective views of two method steps for inserting the ISS implant of FIG. 24; and FIGS. 26A and 26B illustrate top perspective views of two additional method steps for inserting the ISS implant of FIG. 24.

DETAILED DESCRIPTION

Figure 1:
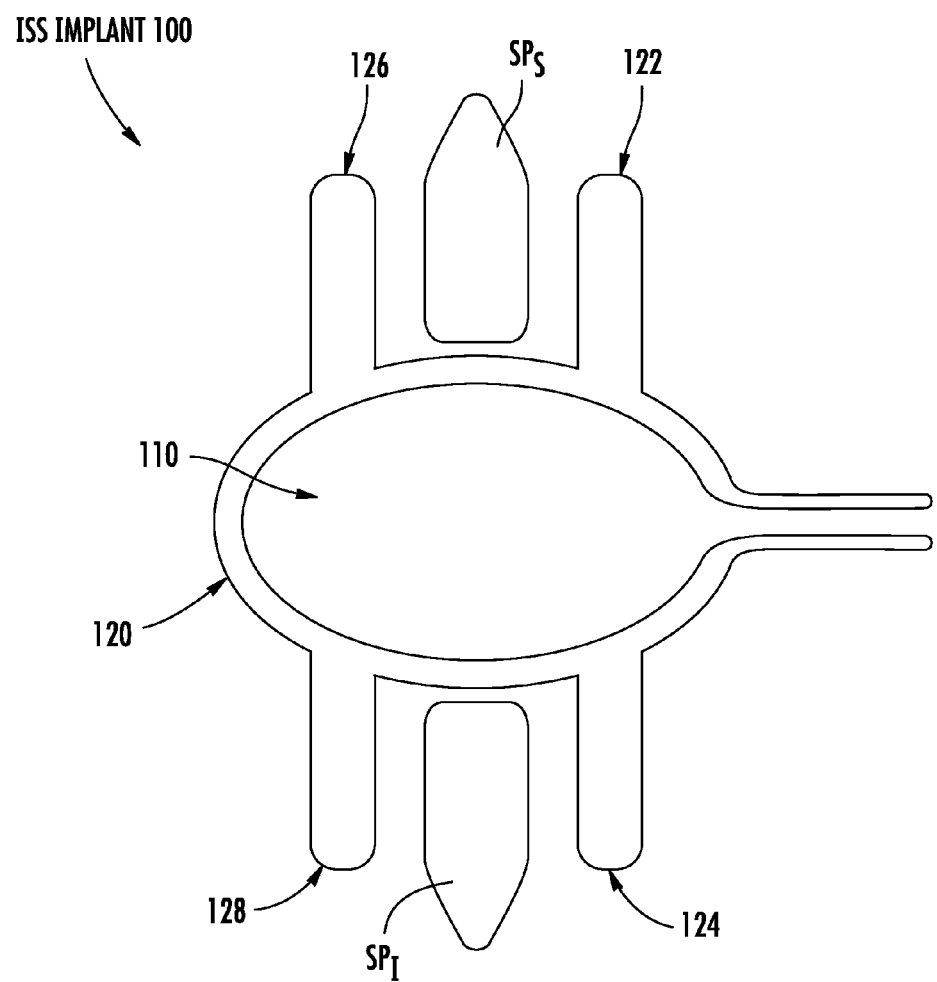
FIG. 1 illustrates a rear elevational view of an ISS implant in accordance with a first preferred embodiment of the present disclosure.

Certain terminology is used in the following description for convenience only and is not limiting. The words "right", "left", "lower" and "upper" designate directions in the drawings to which reference is made. The words "inwardly" or "distally" and "outwardly" or "proximally" refer to directions toward and away from, respectively, the patient's body, or the geometric center of the preferred ISS implants and related parts thereof. The words, "anterior", "posterior", "superior,"

"inferior", "lateral" and related words and/or phrases designate preferred positions, directions and/or orientations in the human body to which reference is made and are not meant to be limiting. The terminology includes the above-listed words, derivatives thereof and words of similar import.

Referring to FIG. 1, an interspinous spacer ("ISS") implant 100 in accordance with a first preferred embodiment of the present disclosure includes an inflatable interior member 110 around which is disposed an exterior member 120. The exterior member 120 is preferably inflatable and includes first, second, third, and fourth protrusions 122, 124, 126, 128, respectively, which serve to limit lateral migration of the implant 100 when the first and third protrusions 122, 126 are disposed on either side of a superior spinous process $SP_S$ and when the second and fourth protrusions 124, 128 are disposed on either side of an inferior spinous process $SP_I$. In the first preferred embodiment, the exterior member 120 is inflatable and the protrusions 122, 124, 126, 128 may also be inflatable or may be formed from solid material. In the first preferred embodiment, the exterior member 120 is formed from a compliant or semi-compliant material, while the interior member 110 can be formed from compliant or non-compliant material. In addition, the protrusions 122, 124, 126, 128 are preferably relatively rigid in the expanded configuration (FIG. 1) and may collapse such that the ISS implant 100 may be introduced between the superior and inferior spinous processes $SP_S$, $SP_I$ through a relatively small diameter cannula (not shown) that is introduced laterally into the interspinous process space in a collapsed configuration (not shown). The interior and exterior members 110, 120 are not limited to being inflatable and may be configured to move from the unexpanded to the expanded configuration and back via a mechanical assembly or a combination of inflatable and mechanical mechanisms.

In operation, and in continuing reference to FIG. 1, the ISS implant 100 is preferably inserted percutaneously between an adjacent pair of spinous processes via a lateral approach through a relatively small cannula in an unexpanded configuration. The inflatable member 110 and the exterior member 120 are then inflated via a biocompatible pressurized fluid and/or gas until the desired spacing between the adjacent spinous processes $SP_S$, $SP_I$ is achieved, wherein the interior member 110 serves as a spacer and the exterior member 120 serves as a securing agent due to the inclusion of the protrusions 122, 124, 126, 128 and as a portion of the spacer.

Referring to FIGS. 2A-2C, an ISS implant 200 in accordance with a second preferred embodiment includes an inflatable member 210 having a longitudinal axis X-X extending between a proximal end and a distal end. First, second, third, and fourth deployable protrusion 222, 224, 226, 228 are disposed on the inflatable member 210 adjacent superior and inferior surfaces at proximal and distal ends of the inflatable member 210, respectively. Each protrusion 222, 224, 226, 228 is preferably comprised of an elongated hollow semi-cylinder and is configured such that, when the inflatable member 210 is in its unexpanded, collapsed or un-inflated configuration, the third and fourth protrusions 226, 228 extend distally along the longitudinal axis X-X and meet to form a cylindrical dilator portion 227, whereas the first and second protrusions 222, 224 extend proximally along the longitudinal axis X-X and meet to form a hollow cylinder portion 223, respectively, which generally protects the inflatable member 210 during insertion. Upon inflation of the inflatable member 210, the protrusions 222, 224, 226, 228 deploy to a configuration in which each is generally perpendicular to the longitudinal axis of the inflatable member 210 to thereby surround the adjacent spinous processes and limit lateral migration of the ISS implant 200. The ISS implant 200 of the second preferred embodiment. The protrusions 222, 224, 226, 228 are no limited to extending generally perpendicularly relative to the longitudinal axis X-X in the expanded configuration and may pinch inwardly toward their tips to engage the spinous processes in the expanded configuration or may stop short of extending generally perpendicularly relative to the longitudinal axis X-X (FIG. 2B) in the expanded configuration. Such orientations may be driven by patient anatomy and/or design of the ISS implant 200 of the second preferred embodiment.

In operation, the ISS implant 200 is preferably inserted percutaneously between an adjacent pair of spinous process via a lateral approach corridor through a relatively small cannula. The undeployed third and fourth protrusions 226, 228 preferably form a cylinder at a proximal end of the implant and serve as a dilator for easing the ISS implant 200 into the desired location via the cylindrical dilator portion 227. The inflatable member 210 is preferably inflated once the ISS implant 200 is in a desired location with the first and second protrusions 222, 224 located on one side of the adjacent spinous processes and the third and fourth protrusions 226, 228 located on the opposite side of the adjacent spinous processes, forcing the protrusions 222, 224, 226, 228 to shift from the unexpanded configuration in which their longitudinal axes are parallel to the longitudinal axis X-X, to the expanded configuration in which their longitudinal axes are perpendicular to the longitudinal axis X-X of the inflatable member 210, such that lateral migration of the ISS implant 200 is limited.

Referring to FIG. 3, an ISS implant 300 in accordance with a third preferred embodiment includes an inflatable member 310 having a longitudinal axis Y-Y extending between a proximal end and a distal end. A relatively solid superior member 320 is disposed on a superior surface of the inflatable member 310 and has a first deployable protrusion 322 and a first bendable portion 321 adjacent the first deployable protrusion 322, as well as a third deployable protrusion 326 and a third bendable portion 325 adjacent the third deployable protrusion 326. Similarly, a relatively solid inferior member 329 is disposed on an inferior surface of the inflatable member 310 and has a second deployable protrusion 324 and a second bendable portion 323 adjacent the second deployable protrusion 324, as well as a fourth deployable protrusion 328 and a fourth bendable portion 327 adjacent the fourth deployable protrusion 328. The bendable portions 321, 323, 325, 327 may be formed by providing a thin portion of material on the superior and inferior members 320, 329 adjacent to the deployable protrusions 322, 324, 326, 328, respectively, resulting in living hinges being formed at the bendable portions 321, 323, 325, 327. Upon inflation of the inflatable member 310, balloon pressure acts upon and deforms the bendable portions 321, 323, 325, 327 to force the protrusions 222, 224, 226, 228 to deploy from an unexpanded configuration in which they are positioned generally parallel to the longitudinal axis Y-Y of the inflatable member 310 to an expanded configuration in which each protrusion 222, 224, 226, 228 is oriented generally perpendicular to the longitudinal axis Y-Y of the inflatable member 310 to contact or position themselves adjacent to sides of the spinous processes.

In operation, and in continuing reference to FIG. 3, the ISS implant 300 is preferably inserted percutaneously between an adjacent pair of spinous process via a lateral approach corridor through a relatively small cannula or surgical pathway. The inflatable member 310 is inflated once the ISS implant 300 is in a desired location, deforming the bendable portions 321, 323, 325, 327 of the upper and lower members 320, 329, thereby forcing the protrusions 322, 324, 326, 328 to shift from the unexpanded configuration in which their longitudinal axes are generally parallel to the longitudinal axis Y-Y of the inflatable member 310, to the expanded configuration in which their longitudinal axes are generally perpendicular to the longitudinal axis Y-Y of the inflatable member 210, such that lateral migration of the ISS implant 200 is limited.

Referring to FIGS. 4A-4D, a variety of balloon-type ISS implants 410, 420, 430, 440 in accordance with a fourth preferred embodiment of the present disclosure include a first U-shaped inflatable member 412 and a second inflatable U-shaped member 414 coupled to one another in a configuration that provides an H-shaped implant 410 in an expanded configuration. The first and second inflatable members 412, 414 can be inflated simultaneously or separately and may include a separate inlet port for each member 412, 414 or a single inlet port with a communication passage between the first and second member 412, 414. FIG. 4B illustrates an ISS implant 420 that includes an inflatable member that assumes an X-shape in the expanded configuration for providing the desired spacing between adjacent spinous processes $SP_S$, $SP_I$ while limiting lateral migration of the implant 420 when fully expanded. FIG. 4C illustrates an ISS implant 430 that includes a U-shaped inflatable member 430 that is folded in an unexpanded configuration prior to implantation and inflation. Upon inflation, the ISS implant 430 assumes the shape of a lower case alpha ($\alpha$) that is well-configured to limit lateral migration of the implant 430 relative to the adjacent spinous processes $SP_S$, $SP_I$. Similarly, FIG. 4D illustrates an ISS implant 440 that includes a generally straight and cylindrical inflatable member 430 that is folded prior to implantation and inflation in an unexpanded configuration. Upon inflation, the ISS implant 440 assumes the shape of a lower case alpha ($\alpha$) that is well-configured to limit lateral migration of the expanded implant 440 relative to the adjacent spinout processes $SP_S$, $SP_I$. For each of the ISS implants 410, 420, 430, 440 of the fourth preferred embodiment, the inflatable member can be filled with either gas, such as oxygen or air, a biocompatible cement, or fluid, such as saline. Further, the inflatable ISS implants 410, 420, 430, 440 can be compliant, semi-compliant, or noncompliant. The ISS implants 410, 420, 430, 440 may be inflated or moved from the unexpanded configuration to the expanded configuration utilizing nearly any biocompatible material that is able to generally fill the ISS implants 410, 420, 430, 440 to reconfigure the implant 410, 420, 430, 440 from the unexpanded configuration to the expanded configuration.

Referring to FIGS. 5A-5D, an ISS implant 500 in accordance with a fifth preferred embodiment includes three linearly-arranged inflatable members 510, 520, 530, including a contralateral balloon 510, a central balloon 520, and an ipsalateral balloon 530. Each inflatable member 510, 520, 530 includes an inlet port that may extend through the center of one or more of the other inflatable members 510, 520, 530. The contralateral balloon 510 and ipsalateral balloon 530 preferably have a similar size and shape, resulting in an expanded height $H_E$ that extends beyond a height $H_I$ of the interspinous space in the expanded configuration and the central balloon 520 preferably has a height $H_C$ that provides a preferred anatomical distance between the adjacent spinous processes $SP_S$, $SP_I$ in the implanted position.

In operation, and in continuing reference to FIGS. 5A-5D, the ISS implant 500 is inserted percutaneously through a lateral approach corridor with each of the inflatable members in a noninflated or unexpanded configuration. Once the implant 500 is disposed in a desired position with respect to the adjacent spinous processes $SP_S$, $SP_I$, the contralateral balloon 510, the central balloon 520, and the ipsalateral balloon 530 are inflated independently of one another and in an order chosen by the user, for example, by inflating the contralateral balloon 510 first, followed by the central balloon 520, and lastly, the ipsalateral balloon 530, as shown in FIGS. 5A-5C. The user may also select the filling material to be used with each of the inflatable members 510, 520, 530, and one or more filling materials may be chosen for one or more of the inflatable members 510, 520, 530. For instance, the user may choose to provide some cushioning between the adjacent spinous processes $SP_S$, $SP_I$ by filling the central balloon 520 with a hydrogel, or may provide a rigid central balloon 520 upon inflation of a noncompliant balloon with air. The contralateral and ipsalateral balloons 510, 530 are configured to extend vertically a greater distance than the central balloon 520 upon inflation such that lateral migration of the ISS implant 500 is limited. Alternatively, the ISS implant 500 may include a three chamber single balloon as opposed to the preferred three separate inflatable members 510, 520, 530. In addition, the inflatable members 510, 510, 530 may be filled with variable stiffness materials to tailor the elasticity of the inflatable members 510, 520, 530 in the expanded configuration to provide a rigid stop between the spinous processes $SP_S$, $SP_I$ or to provide compliance or damped motion between the spinous processes $SP_S$, $SP_I$.

Referring to FIG. 6A-7B, an ISS implant 600 in accordance with a sixth and seventh preferred embodiment includes a central, generally rigid rod member 630 extending along a longitudinal axis Z-Z having a proximal end and a distal end and a spacer portion 610, which may be an inflatable, semi-compliant balloon member 610 or a solid form of rigid, elastomeric, or dampening material 610' disposed about the rod member 630. Disposed axially about the central rod member 630 at the distal end is a first plurality of nitinol wires 620 and disposed axially about the central rod member 630 at the proximal end is a second plurality of nitinol wires 625. The first and second plurality of nitinol wires 620, 625 include a pre-tensioned, insertion configuration (FIG. 6A), in which their longitudinal axes are generally parallel to the longitudinal axis Z-Z of the ISS implant 600, and an untensioned, implanted configuration (FIG. 6B-7B), in which their longitudinal axes are generally perpendicular to the longitudinal axis Z-Z of the ISS implant 600.

In operation, and in continuing reference to FIGS. 6A-7B, the ISS implant 600 is preferably housed within a cylindrical tube or cannula 605 during insertion, such that the longitudinal axes of the first and second plurality of nitinol wires 620, 625 are generally parallel to the longitudinal axis Z-Z of the ISS implant 600. The cylindrical tube 605 is preferably, percutaneously inserted through a lateral approach corridor to a position between the adjacent spinous processes. The ISS implant 600 may alternatively be implanted without the cannula 605 by urging the implant 600 directly through the patient's soft tissue to the implantation site. Following implantation, the cylindrical tube or cannula 605 is removed from the patient, leaving the spacer portion 610 positioned between the adjacent spinous processes $SP_S$, $SP_I$. As the cylindrical tube or cannula 605 is retracted, the first and second plurality of nitinol wires 620, 625 return to their unstressed or expanded configuration, in which their longitudinal axes are generally perpendicular to the longitudinal axis Z-Z of the ISS implant 600, thereby limiting lateral migration of the ISS implant 600 with respect to the adjacent spinous processes $SP_S$, $SP_I$. In the case in which the spacer portion 610 is inflatable, it is then inflated with a gas, solid, or liquid material to provide the desired characteristic of the inflatable member 610 (rigid or elastic). If the spacer portion 610' is not inflatable, the inflating step is generally unnecessary. In such an arrangement, the compliance of the spacer element 610' can be influenced by both choice of material as well as the inclusion of an exemption 612 between a central rod member 630' and the spacer portion 610', as is best shown in FIG. 7.

Referring to FIGS. 8A and 8B, an ISS implant 700 in accordance with an eighth preferred embodiment includes a central piston member 730 having a protruding distal stop surface 732. Disposed about the central piston member 730 is a flexible cylindrical spacer portion 710. Disposed about the central piston member 730 and adjacent to the flexible spacer portion 710 is a generally rigid tubular member 720 having a proximal stop surface 722 at its distal end. The flexible spacer member 710 is preferably sandwiched between the distal stop surface 732 and the proximal stop surface 722 and the rigid tubular member 720 is slidably translatable over the central piston member 730. In an unexpanded configuration, the distal stop surface 732 and the proximal stop surface 722 are spaced at an unexpanded length $L_U$ that is typically at least as long as a length $L_F$ of the flexible spacer portion 710.

In operation, and in continuing reference to FIG. 8, the ISS implant 700 is preferably inserted percutaneously through a lateral approach corridor, preferably through a cannula, until the flexible spacer portion 710 is generally centered between the adjacent pair of spinous processes $SP_S$, $SP_I$. The central piston member 730 is then retracted with respect to the rigid tubular member 720, thereby reducing the unexpanded length $L_U$ such that the flexible spacer portion 710 is squeezed between the distal stop surface 732 and the proximal stop surface 722 and the flexible spacer portion is forced to fold over and surround the lateral aspects of the adjacent spinous processes $SP_S$, $SP_I$. The rigid tubular member 720 is then locked with respect to the central piston member 730 such that the ISS implant 700 is limited from lateral migration relative to the spinous processes $SP_S$, $SP_I$. In this expanded configuration, the distal stop surface 732 and the proximal stop surface 722 are spaced at an expanded length $L_E$ that is smaller than the length $L_F$ of the flexible spacer portion 710 and the flexible spacer portion 710 has an expanded height $H_E$ that is greater than a height $H_S$ of the distal and proximal stop surfaces $H_D$, $H_P$.

Referring to FIG. 9, an ISS implant 800 in accordance with a ninth preferred embodiment is comprised of an inflatable balloon-type implant 800 having a central portion 800a with a reduced size or height $H_C$ with respect to first and second enlarged end portions $H_{EP}$ in an expanded configuration. The ISS implant 800 further includes a cannulated interior configured to slide over a guidewire 810. In operation, the guidewire 810 is inserted through the posterior of a patient and glides along the interspinous space between the adjacent spinous processes $SP_S$, $SP_I$, preferably without perforating the supraspinous ligament SSL. The interspinous ligament ISL is then preferably perforated by the guidewire 810. The ISS implant 800 is then inserted over the guidewire 810 into the interspinous space and inflated such that the enlarged portions 800b of the ISS implant 800 are positioned contralaterally and ipsilaterally of the interspinous space to limit movement of the ISS implant 800 relative to the spinous processes $SP_S$, $SP_I$.

Figure 10:
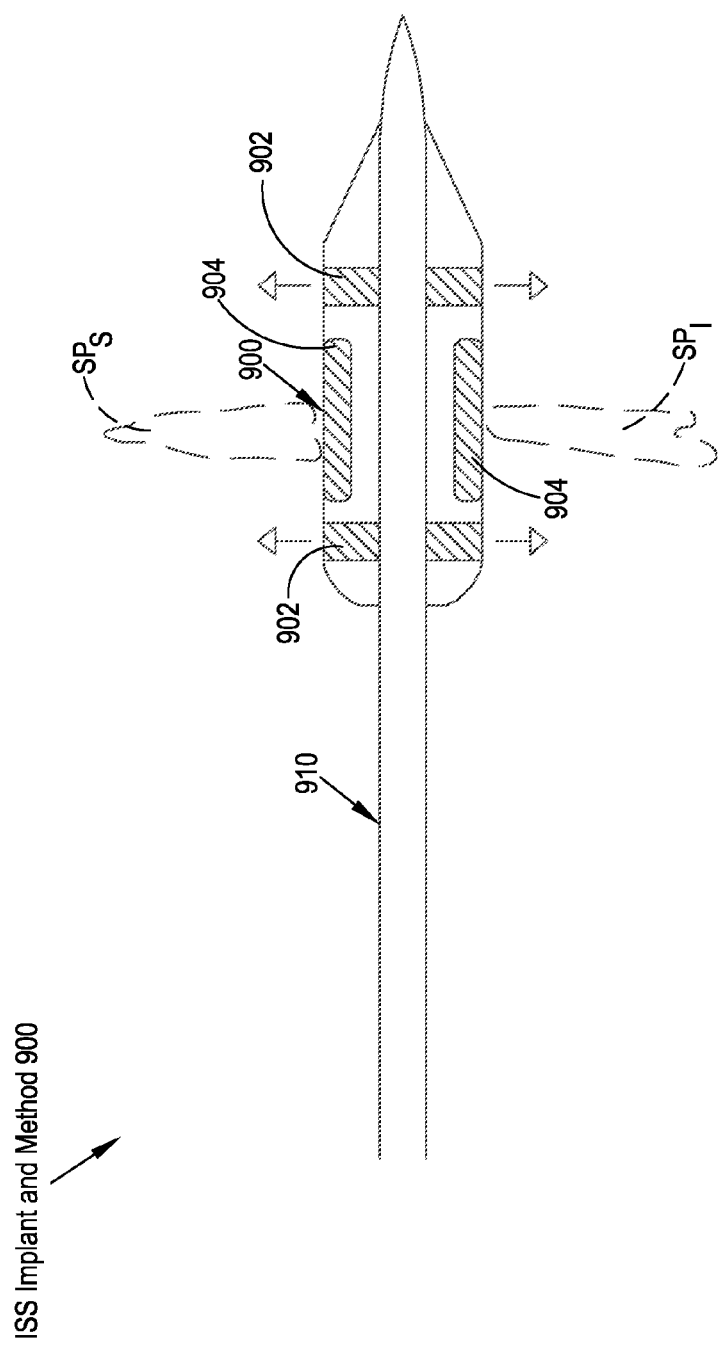
FIG. 10 illustrates a rear elevational view of an ISS implant in accordance with a tenth preferred embodiment of the present disclosure.

Referring to FIG. 10, an ISS implant 900 in accordance with a tenth preferred embodiment is comprised of an inflatable implant configured for percutaneous insertion over a guidewire 910. The ISS implant 900 includes a cannulated interior configured for delivering the ISS implant 900 over the guidewire 910. The guidewire 910 is preferably inserted laterally into the interspinous space between the adjacent spinous processes $SP_S$, $SP_I$ and perforates the interspinous ligament. The ISS implant 900 is then delivered over the guidewire 910 into position between the spinous processes $SP_S$, $SP_I$. The ISS implant 900 preferably includes lateral inflatable members 902 that are preferably configured to expand to surround the lateral aspects of the spinous processes $SP_S$, $SP_I$ such that lateral migration of the ISS implant 900 is limited. Alternatively, the lateral members 902 may be mechanically deployable. The ISS implant 900 also preferably includes a dampening member 904 generally centrally located on an exterior surface that contacts the adjacent spinous processes $SP_S$, $SP_I$ in the implanted position.

Figure 11:
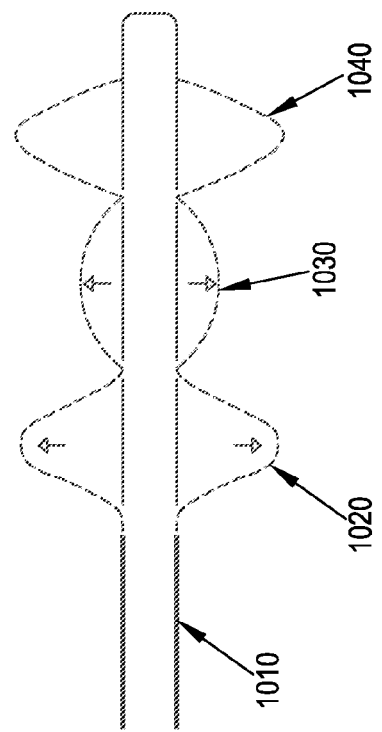
FIG. 11 illustrates a rear elevational view of an ISS implant in accordance with an eleventh preferred embodiment of the present disclosure.

In reference to FIG. 11, an ISS implant 1000 in accordance with an eleventh preferred embodiment includes a rigid catheter 1010 around which is disposed a proximal expandable member 1020, a central expandable member 1030, and a distal expandable member 1040. The proximal and distal expandable members 1020, 1040 may assume the form of a stent, a balloon-type expandable member, a self-expanding foam structure that expands when resistance provided by the catheter 1010 is removed, locking-stopping bumps or toruses, or members that are expandable by a pulling mechanism. The central expandable member 1030 may assume the form of a balloon or a multi-lumen balloon having differing compliances, or a self-expanding foam structure. In operation, the ISS implant 1000 is preferably inserted percutaneously from a lateral approach corridor and the proximal, central, and distal expandable members 1020, 1030, 1040 are expanded. In the eleventh preferred embodiment in which the proximal and distal expandable members 1020, 1040 are stent-like expandable forms, the stent portions 1020, 1040 may be formed by removal of material and the formation of a stent-pattern in the catheter 1010 itself, or stent members may be applied over the catheter 1010 and around a portion that houses a deployable balloon 1030 for expanding the stent portions 1020, 1040. In the preferred embodiment, the expandable members 1020, 1030, 1040 are enlarged by a pulling mechanism.

In reference to FIG. 12, an ISS implant 1100 in accordance with a twelfth preferred embodiment includes a cross-section of circular, oval, or rectangular and is configured for insertion between the adjacent spinous processes $SP_S$, $SP_I$ while enclosed within a tubular insertion sleeve 1111. The ISS implant 1100 includes a pair of proximal wings 1110, 1112 and a pair of distal wings (not shown). Each pair of wings 1110, 1112 is configured to be rotatable about a joint (not shown) in a plane that is generally parallel to the medial plane. In the same planes proximal and distal, a rod shaped element (not shown) is connected with a rotatable central shaft 1130. Upon rotation of the central shaft 1130, the rod shaped element 1130 forces the proximal and distal pairs of wings 1110, 1112 to rotate about their joints and extend into a position in which they serve as lateral migration stops to limit movement of the ISS implant 1100 relative to the spinous processes $SP_S$, $SP_I$.

Referring to FIGS. 13A-14B, an ISS implant 1200 of a thirteenth preferred embodiment includes an implant body 1210, a central rod 1220 having proximal and distal ends and a longitudinal axis M-M extending therebetween. A first wing 1232 and a second wing 1234 are preferably coupled to the central rod 1220 near the proximal end, and a third wing 1236 and a fourth wing 1238 are preferably coupled to the rotatable central rod 1220 near the distal end. The wings 1232, 1234, 1236, 1238 are preferably formed of a resilient or deformable material and are configured to assume an undeployed state or configuration (FIGS. 13A and 13B), in which they are at least partially wrapped around the central rod 1220, as well as a deployed state (FIGS. 13C-14B), in which they are unwound from the central rod 1220 via rotation of the central rod 1220 such that the wings 1232, 1234, 1236, 1238 are deployed to extend away from the implant body 1210 through a first slot 1242, a second slot 1244, a third slot 1246, and a fourth slot 1248, respectively, formed through the outer surface of the implant body 1210 and positioned so as to accommodate the deployment of the wings 1232, 1234, 1236, 1238 away from the outer surface of the implant body 1210. In operation, the ISS implant 1200 is preferably inserted percutaneously between the adjacent spinous processes $SP_S$, $SP_I$ via a lateral approach corridor, typically through a cannula (not shown). An instrument engages an engagement feature 1222 on the proximal end of the central rod 1220 and is rotated to turn the central rod 1210 and, thereby, undeform or unstress the wings 1232, 1234, 1236, 1238 to thereby allow them to deploy through the slots 1242, 1244, 1246, 1248, respectively and serve as lateral migration stops for the positioning of the ISS implant 1200 with respect to the interspinous space and the adjacent spinous processes $SP_S$, $SP_I$. Alternatively, as is shown in FIGS. 15A and 15B, the shaft 1222 member is formed to include longitudinal slots 1221 through an external sleeve 1223 that allow the wing pairs 1236, 1238, and the wing pairs 1232, 1234, to be formed as unitary elements and to be positioned generally within the bounds of the external sleeve 1223 in the undeployed configuration.

In reference to FIGS. 16A-16D, an ISS implant 1300 in accordance with a fourteenth preferred embodiment includes an implant body 1310, a central shaft 1320 having a proximal end and a distal end, wherein the proximal end further includes an instrument engagement feature 1360 and the central shaft 1320 further includes a first worm gear 1322 disposed near its proximal end and operatively connected to a first pair of wings 1332, 1334 and a second worm gear 1324 disposed at its distal end and operatively connected to a second pair of wings 1336, 1338. The first and second pairs of wings 1332, 1334, 1336, 1338 are operatively connected to the first and second worm gears 1322, 1324, respectively, via the inclusion at the base of each wing 1332, 1334, 1336, 1338 of a snail gear 1352, 1354, 1356, 1358, respectively. In operation, the ISS implant 1300 is preferably inserted percutaneously through a lateral approach corridor and placed between the spinous processes $SP_S$, $SP_I$. An instrument (not shown) engages and is turned to rotate the instrument engagement feature 1360 and thereby force the first and second worm gears 1322, 1324 to engage the snail gears 1352, 1354, 1356, 1358 to thereby deploy the wings 1332, 1334, 1336, 1338 through a range of approximately ninety degrees (90°), from a position in which the longitudinal axes of the wings 1332, 1334, 1336, 1338 are generally parallel to a longitudinal axis N-N of the implant body 1310 to a position in which the longitudinal axes of the wings 1332, 1334, 1336, 1338 are generally perpendicular to the longitudinal axis N-N of the implant body 1310.

In reference to FIG. 17A-17D, an ISS implant 1400 in accordance with a fifteenth preferred embodiment includes an implant body 1410 having a longitudinal axis O-O extending between a proximal end and a distal end and a central rod 1480 disposed through the center of the implant body 1410 that extends along the longitudinal axis O-O. The central rod 1480 is operatively coupled at its proximal end to a proximal turning wheel 1450 and is operatively coupled at its distal end to a distal turning wheel 1460 such that, upon rotation of the proximal turning wheel 1450, i.e., via the rotation of an instrument temporarily coupled to an instrument engagement feature (not shown) formed at the proximal end of the proximal turning wheel 1450, the proximal turning wheel 1450, the central rod 1480, and the distal turning wheel 1460 are each forced to rotate with respect to the implant body 1410. In the preferred embodiment, the distal turning wheel 1460 includes a bullet nosed tip to ease the insertion of the ISS implant 1400 and/or apply distraction during the insertion of the ISS implant 1400. A first proximal slot 1422 and a second proximal slot 1424 are preferably formed adjacent the proximal end of the implant body 1410 and the longitudinal axes of the first and second proximal slots 1422, 1424 are oriented generally perpendicular to the longitudinal axis O-O of the implant body 1410. Similarly, a first distal slot 1426 and a second distal slot 1428 are formed adjacent the distal end of the implant body 1410 and the longitudinal axes of the first and second distal slots 1426, 1428 also generally oriented perpendicular to the longitudinal axis O-O of the implant body 1410. First and second proximal wings 1432, 1434 and first and second distal wings 1436, 1438 are positioned in the first and second proximal slots 1422, 1424 and the first and second distal slots 1426, 1428, respectively. Each of the first and second proximal wings 1432, 1434 and the first and second distal wings 1436, 1438 includes a post 1431, 1433, 1435, 1437, respectively, that protrudes into a slot 1462, 1464, 1466, 1468, respectively, formed on the interior surface of the proximal and distal turning wheels 1450, 1460. The wings 1432, 1434, 1436, 1438 are preferably generally contained within the slots 1462, 1464, 1466, 1468 in the unexpanded configuration and extend from the slots 1462, 1464, 1466, 1468 in the expanded configuration.

In operation, and in continuing reference to FIGS. 17A-17D, the ISS implant 1400 is preferably inserted percutaneously through a lateral approach corridor such that the implant body 1410 is positioned between the spinous processes $SP_S$, $SP_I$. An instrument is coupled to the instrument engagement feature on the proximal turning wheel 1450 and is rotated, forcing the proximal turning wheel 1450, the central rod 1480, and the distal turning wheel 460 to rotate, preferably approximately ninety to one hundred degrees (90-100°), with respect to the implant body 1410. During rotation of the proximal turning wheel 1450, the central rod 1480, and the distal turning wheel 1460, the posts 1431, 1433, 1435, 1437 are forced to interact with, preferably slide within, the rotating slots 1462, 1464, 1466, 1468 formed on the interior surface of the proximal and distal turning wheels 1450, 1460, thereby forcing the wings 1432, 1434, 1436, 1438 to translate within the first and second proximal slots 1422, 1424 and the first and second distal slots 1426, 1428 formed at the proximal and distal ends of the implant body 1410, thereby deploying the wings 1432, 1434, 1436, 1438 outwardly with respect to the exterior surface of the implant body 1410 to serve as lateral migration stops to limit migration of the ISS implant 1400 with respect to the spinous processes $SP_S$, $SP_I$.

In reference to FIG. 18, an ISS implant 1500 in accordance with a sixteenth preferred embodiment includes a balloon-type element 1510 disposed about a mechanically expandable ISS implant 1400 such as that of the fifteenth preferred embodiment. The balloon-type element 1510 may also be disposed about ISS implants 1300, 1200, 1100 that are similar to the twelfth, thirteenth and fourteenth preferred embodiments. For the sake of illustration, the ISS implant 1500 includes the balloon-type element 1510 and the ISS implant 1400 of the fifteenth preferred embodiment, but may assume a variety of different configurations. The inflatable balloon-type element 1510 is disposed about the implant body 1410 in a position such that, upon implantation, the balloon-type element 1510 is positioned between the adjacent spinous processes $SP_S$, $SP_I$. The balloon-type element 1510 may be pre-inflated prior to implantation of the ISS implant 1500 or may be inflated subsequent to insertion of the ISS implant 1500 between the adjacent spinous processes $SP_S$, $SP_I$. The inclusion of the balloon-type element 1510 enables the ISS implant 1500 to achieve significant bony contact to the spinous processes $SP_S$, $SP_I$, resulting in a contact surface with generally equally distributed stress for the bone and a limitation of stress peaks or risers, which may in some cases lead to bone resorption and loss of spacer height, while at the same time absorbing a portion of the stress imparted to the implant body 1510. The balloon-type element 1510 may be filled with gas or liquid or solid dampening material. A liquid material that is chosen to cure to a hard material subsequent to implantation and inflation can maximize surface area of contact between the spinous processes $SP_S$, $SP_I$ and the ISS implant 1500. The choice of a softer fill material, such as silicone or polyurethane, enables the absorption of stress and the dampening of loads imparted to the portions of the spinous processes $SP_S$, $SP_I$ that contact the ISS implant 1500, thereby decreasing the risk or adaptation or erosion of the spinous processes $SP_S$, $SP_I$.

In reference to FIG. 19, an ISS implant 1600 in accordance with a seventeenth preferred embodiment includes two W-folded plates that serve as a dampening spacer between the adjacent spinous processes $SP_S$, $SP_I$. Features of the ISS implant 1600 can further be combined with the ISS implants 1100, 1200, 1300, 1400 twelfth, thirteenth, fourteenth and fifteenth preferred embodiments in that a form similar to the two W-folded plates can be formed into or replace the spacer bodies of the ISS implants 1100, 1200, 1300, 1400.

Figure 20:
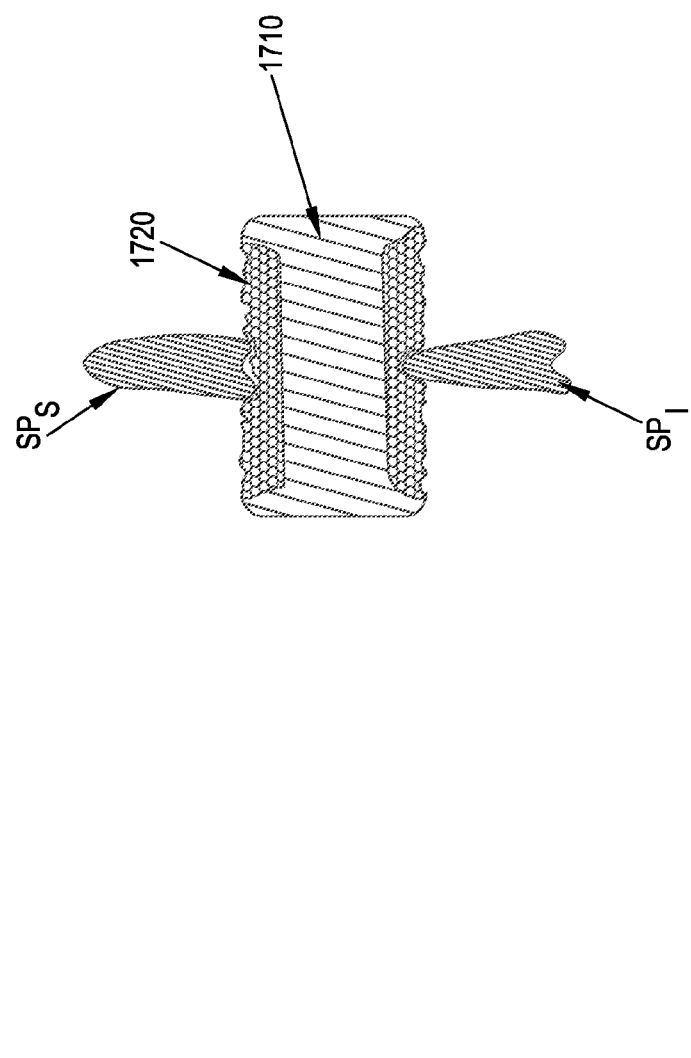
FIG. 20 illustrates a rear cross-sectional view of an ISS implant in accordance with an eighteenth preferred embodiment of the present disclosure.

Referring to FIG. 20, an ISS implant 1700 in accordance with an eighteenth preferred embodiment includes a spacer portion 1710 with a hard foam coating 1720 on at least the portions of the spacer portion 1710 that come into contact with the adjacent spinous processes $SP_S$, $SP_I$. The hard foam 1720 is compressible such that the surface area of contact between the spinous processes $SP_S$, $SP_I$ and the ISS implant 1700 is maximized to provide an anatomical fit and a generally equal distribution of stress to the spinous processes $SP_S$, $SP_I$ in the implanted position.

In reference to FIG. 21, an ISS implant 1800 of a nineteenth preferred embodiment includes a spacer portion 1810 and a flexible membrane 1820 filled with small granulae surrounding at least the portions of the spacer portion 1810 that come into contact with the adjacent spinous processes $SP_S$, $SP_I$. The granulae 1820 can be formed using materials such as biocompatible polymers such as PEEK, PEKK, polyurethane, etc. Under load, the individual granules within the flexible membrane 1820 that experience the largest amount of force are displaced laterally such that the anatomy of the spinous processes $SP_S$, $SP_I$ is accommodated and the surface area of contact between the spinous processes $SP_S$, $SP_I$ and the ISS implant 1800 is maximized. The inclusion of a flexible membrane 1820 filled with granulae can further be incorporated into the design of others of the preferred ISS implants, which were described above.

Referring to FIGS. 22A and 22B, an ISS implant 1900 in accordance with a twentieth preferred embodiment includes a spacer portion 1810 and a flexible membrane filled with fiber-shaped material 1920 surrounding at least the portions of the spacer portion 1910 that come into contact with interspinous processes $SP_S$, $SP_I$. The fiber-shaped material 1920 can be formed using materials such as biocompatible polymers such as PEEK, PEKK, and polyurethane. Under load, the individual fibers within the flexible membrane or fiber-shaped material 1920 that experience the largest amount of force are displaced laterally such that the precise anatomy of the spinous processes $SP_S$, $SP_I$ is generally accommodated and the surface area of contact between the spinous processes $SP_S$, $SP_I$ and the ISS implant 1900 is maximized. The inclusion of the flexible membrane filled with fiber-shaped material 1920 can further be incorporated into the design of the ISS implants of the above-described preferred embodiments.

Figure 23:
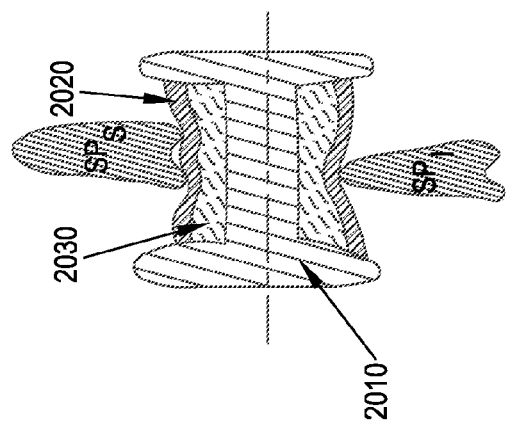
FIG. 23 illustrates a rear cross-sectional view of an ISS implant in accordance with an twenty-first preferred embodiment of the present disclosure.

Referring to FIG. 23, an ISS implant 2000 in accordance with a twenty-first preferred embodiment includes a rigid spacer portion 2010 and a flexible membrane 2020 that surrounds at least the portions of the spacer portion 2010 that come into contact with the adjacent spinous processes $SP_S$, $SP_I$. A sealed chamber is provided between the spacer portion 2010 and the flexible membrane 2020 that can be filled with bone cement 2030 upon insertion of the ISS implant 1900 between the spinous processes $SP_S$, $SP_I$. As the chamber is filled, the cement 2030 is distributed in such a way that the surface area of contact between the ISS implant 2000 and the spinous processes $SP_S$, $SP_I$ is maximized. Following implantation, the flexible membrane 2020 is configured to absorb some load and provide a dampening aspect to the ISS implant 2000. The inclusion of a flexible membrane 2020 and a sealed chamber between the spacer portion 2010 and the flexible membrane 2020 can further be incorporated into the design of ISS implants of nearly any of the above-described preferred embodiments.

Referring to FIGS. 24A-26B, an ISS implant 2100 and corresponding method in accordance with a twenty-second preferred embodiment is comprised of an hourglass-shaped balloon-type member 2100 configured to be introduced percutaneously between the adjacent spinous processes $SP_S$, $SP_I$ in a deflated or unexpanded configuration and, upon desired positioning with respect to the adjacent spinous processes $SP_S$, $SP_I$, filled with a hardening fluid to a point at which a middle portion 2100a reaches a diameter d adequate to treat the indication or to generally recreate an anatomically accurate distance between the adjacent spinous processes $SP_S$, $SP_I$. An enlarged diameter D of lateral portions 2100b of the ISS implant 2100 serve as lateral migration stops to generally limit lateral movement of the ISS implant 2100 relative to the spinous processes $SP_S$, $SP_I$.

Referring to FIGS. 23A-24B, in operation, a guidewire 2110 is placed between the adjacent spinous processes $SP_S$, $SP_I$ via a lateral approach corridor. In reference to FIG. 25B, a cannulated protection sleeve 2120 is placed over the guidewire 2110 until the distal end of the cannulated protection sleeve 2120 advances distally past the interspinous space between the adjacent spinous processes $SP_S$, $SP_I$ by approximately two centimeters (2 cm). The guidewire 2110 is then removed. In reference to FIG. 26A, the ISS implant 2100, in a folded and unexpanded configuration and attached to an implant cannula 2130 (shown in FIG. 26B), is inserted distally through the cannulated protection sleeve 2120 until the distal end of the ISS implant 2100 reaches the distal end of the cannulated protection sleeve 2120, at which point the cannulated protection sleeve 2120 is removed. In reference to FIG. 26B, a hardening radiopaque material in a liquid phase, such as liquid silicone, PMMA, or another liquid, is injected into the ISS implant 2100 through the implant cannula 2130 until a specific pressure is reached, such as a pressure at which it is known that the ISS implant 2100 is inflated to a specific size and in contact with a desired amount of surface area of the adjacent spinous processes $SP_S$, $SP_I$. Once the liquid filling material has hardened, the implant cannula 2130 is broken away from the ISS implant 2100 and removed from the patient.

It will be appreciated by those skilled in the art that changes could be made to the embodiments described above without departing from the broad inventive concept thereof. It is understood, therefore, that this disclosure is not limited to the particular embodiments disclosed, but it is intended to cover modifications within the spirit and scope of the present disclosure as defined by the present description.

What is claimed:

1. An interspinous process spacer for implantation in an interspinous space between a superior spinous process and an inferior spinous process, the interspinous process spacer comprising:
   a balloon-like body comprising an inflatable interior member and an inflatable exterior member disposed around the inflatable interior member, the balloon-like body having a distal end, a proximal end, and a longitudinal axis extending between the proximal and distal ends, the balloon-like body being arrangeable in an unexpanded configuration and an expanded configuration;
   the inflatable exterior member including:
      a first and a separate third deployable protrusion mounted proximate the proximal end of the balloon-like body and each having an elongate axis, the third deployable protrusion generally opposite the first deployable protrusion, wherein the first deployable protrusion and the third deployable protrusion are comprised of an elongated hollow semi-cylinder and extend proximally along the longitudinal axis of the balloon-like body in the unexpanded configuration to cover and protect a portion of the balloon-like body; and
      a second and a separate fourth deployable protrusion mounted proximate the distal end of the balloon-like body and each having an elongate axis, the fourth deployable protrusion generally opposite the second deployable protrusion, wherein the second deployable protrusion and the fourth deployable protrusion are comprised of an elongated hollow semi-cylinder and extend distally along the longitudinal axis of the balloon-like body in the unexpanded configuration to cover and protect another portion of the balloon-like body;
      wherein the elongate axes of the first, second, third, and fourth deployable protrusions are oriented generally parallel to the longitudinal axis in the unexpanded configuration and generally perpendicular to the longitudinal axis in the expanded configuration
      wherein inflating the exterior member deploys the first, second, third, and fourth deployable protrusions.

2. The interspinous process spacer of claim 1 wherein at least one deployable protrusion is inflatable.

3. The interspinous process spacer of claim 1 wherein the inflatable exterior member is formed from one of a compliant material or a semi-compliant material, and wherein the interior member is formed from one of compliant material or non-compliant material.

4. The interspinous process spacer of claim 1 wherein inflating the exterior member inflates the first, second, third, and fourth deployable.

5. The interspinous process spacer of claim 1 wherein at least one deployable protrusion is relatively rigid in the expanded configuration.

6. The interspinous process spacer of claim 1 wherein the first deployable protrusion and the second deployable protrusion pinch inwardly when expanded.

7. The interspinous process spacer of claim 1 wherein an inflatable component is inflated with a biocompatible fluid or biocompatible gas, wherein the inflatable component comprises at least one from among a group consisting of the inflatable interior member, the inflatable exterior member, the first deployable protrusion, the second deployable protrusion, the third deployable protrusion, and the fourth deployable protrusion.

8. The interspinous process spacer of claim 1 wherein at least one protrusion is formed from solid material.

9. The interspinous process spacer of claim 1 further comprising: a relatively solid member disposed on a surface of the balloon-like body; a first bendable portion distally adjacent to the relatively solid member and adjacent to the first deployable protrusion, the bendable portion acting as a hinge between the relatively solid member and the first deployable protrusion; and a second bendable portion proximally adjacent to the relatively solid member and adjacent to the second deployable protrusion, the bendable portion acting as a hinge between the relatively solid member and the second deployable protrusion.

10. An interspinous process spacer for implantation in an interspinous space between a superior spinous process and an inferior spinous process, the interspinous process spacer comprising:
   a symmetrical pre-shaped balloon-like body having a distal end, a proximal end, a longitudinal axis extending between the proximal and distal ends, the balloon-like body being arrangeable in an unexpanded configuration and an expanded configuration,
   a first and a separate third deployable protrusion mounted proximate the proximal end and each having an elongate axis, the third deployable protrusion generally opposite the first deployable protrusion, wherein the first deployable protrusion and the third deployable protrusion are comprised of an elongated hollow semi-cylinder and extend proximally along the longitudinal axis of the balloon-like body in the unexpanded configuration to cover and protect a portion of the balloon-like body; and
   a second and a separate fourth deployable protrusion mounted proximate the distal end and each having an elongate axis, the fourth deployable protrusion generally opposite the second deployable protrusion, wherein the second deployable protrusion and the fourth deployable protrusion are comprised of an elongated hollow semi-cylinder and extend distally along the longitudinal axis of the balloon-like body in the unexpanded configuration to cover and protect another portion of the balloon-like body;
   wherein the elongate axes of the first second, third and fourth deployable protrusions are oriented generally parallel to the longitudinal axis in the unexpanded configuration and generally perpendicular to the longitudinal axis in the expanded configuration.

11. The interspinous process spacer of claim 10 wherein the symmetrical pre-shaped balloon-like body further comprises an H-shaped inflatable body.

12. The interspinous process spacer of claim 11 wherein the H-shaped inflatable body further comprises: a first U-shaped inflatable member having a distal end, a proximal end, and a longitudinal axis extending between the proximal and distal ends, the first U-shaped inflatable member being arrangeable in an unexpanded configuration and an expanded configuration; and a second U-shaped inflatable member having a distal end, a proximal end, and a longitudinal axis extending between the proximal and distal ends, the second U-shaped inflatable member being arrangeable in an unexpanded configuration and an expanded configuration, and the second U-shaped inflatable member in coupled in opposition and adjacent to the first U-shaped inflatable member along the longitudinal axis such that the first U-shaped inflatable member and the second U-shaped inflatable member together form the H-shaped balloon-like body.

13. The interspinous process spacer of claim 12 wherein the symmetrical pre-shaped balloon-like body further comprises an X-shaped inflatable body.

14. The interspinous process spacer of claim 13 wherein the H-shaped inflatable body comprises a single inflatable member being arrangeable in an unexpanded configuration and an expanded configuration.

15. The interspinous process spacer of claim 12 wherein the first U-shaped inflatable member can be inflated separately from the second U-shaped inflatable member.

16. The interspinous process spacer of claim 12 wherein the first U-shaped inflatable member is in communication with the second U-shaped inflatable member such that the first U-shaped inflatable member and the second U-shaped inflatable member can be inflated simultaneously.

17. The interspinous process spacer of claim 11 wherein the H-shaped inflatable body comprises a single inflatable member being arrangeable in an unexpanded configuration and an expanded configuration.

18. The interspinous process spacer of claim 10 further comprising three linearly-arranged inflatable members wherein: the longitudinal axis extending between the proximal and distal ends comprises a central balloon; the distal end comprises a contralateral balloon that extends beyond the height of the interspinous space in the expanded configuration; and the proximal end comprises a ipsalateral balloon that extends beyond the height of the interspinous space in the expanded configuration.

19. The interspinous process spacer of claim 18 wherein the central balloon can be inflated separately from the ipsalateral balloon and the contralateral balloon.

20. The interspinous process spacer of claim 18 wherein the central balloon, the ipsalateral balloon, and the contralateral balloon can each be inflated separately from the other.

21. The interspinous process spacer of claim 18 wherein the contralateral balloon is in communication with the ipsalateral balloon such that the contralateral balloon and the ipsalateral balloon can be inflated simultaneously.

22. The interspinous process spacer of claim 21 wherein the contralateral balloon and the ipsalateral balloon are in communication with the central balloon such that the contralateral balloon and the ipsalateral balloon can be inflated simultaneously with the central balloon.

23. The interspinous process spacer of claim 10 wherein the symmetrical pre-shaped balloon-like body further comprises an alpha-shaped inflatable body.

24. The interspinous process spacer of claim 10 wherein the symmetrical pre-shaped balloon-like body comprises a three-chamber inflatable body wherein: the longitudinal axis extending between the proximal and distal ends comprises a central chamber of the three-chamber inflatable body; the distal end comprises a contralateral chamber of the three-chamber inflatable body, wherein the contralateral chamber extends beyond the height of the interspinous space in the expanded configuration; and the proximal end comprises a ipsalateral chamber of the three-chamber inflatable body, wherein the ipsalateral chamber extends beyond the height of the interspinous space in the expanded configuration.

* * * * *